US008734373B2

(12) United States Patent  
Esteron

(10) Patent No.: US 8,734,373 B2  
(45) Date of Patent: May 27, 2014

(54) ASSEMBLY, DEVICE KIT AND METHOD FOR PREPARING PLATELET-RICH PLASMA (PRP)

(76) Inventor: Aaron Esteron, Holon (IL)

( * ) Notice: Subject to any disclaimer, the term of this patent is extended or adjusted under 35 U.S.C. 154(b) by 58 days.

(21) Appl. No.: 13/264,902

(22) PCT Filed: Apr. 19, 2010

(86) PCT No.: PCT/IL2010/000309  
§ 371 (c)(1),  
(2), (4) Date: Oct. 17, 2011

(87) PCT Pub. No.: WO2010/122548  
PCT Pub. Date: Oct. 28, 2010

(65) Prior Publication Data  
US 2012/0045424 A1   Feb. 23, 2012

Related U.S. Application Data

(60) Provisional application No. 61/202,934, filed on Apr. 21, 2009.

(51) Int. Cl.  
*A61M 37/00*   (2006.01)
(52) U.S. Cl.  
USPC ............................................ 604/6.1
(58) Field of Classification Search  
USPC ............................................ 604/6.1  
See application file for complete search history.

(56) References Cited

U.S. PATENT DOCUMENTS 3,607,093 A * 9/1971 Stone ........................... 422/422
5,089,146 A * 2/1992 Carmen et al. ............... 210/782
5,258,127 A * 11/1993 Gsell et al. ................... 210/767

(Continued)

FOREIGN PATENT DOCUMENTS

| EP | 0442114 A2 | 8/1991 |
| WO | 91/04088 A1 | 4/1991 |
| WO | 2004018078 A1 | 3/2004 |
| WO | 2005065269 A2 | 7/2005 |

OTHER PUBLICATIONS

International Search Report dated Mar. 21, 2011 in corresponding International Application No. PCT/IL2010/000309.

(Continued)

*Primary Examiner* — Susan Su  
*Assistant Examiner* — Guy K Townsend  
(74) *Attorney, Agent, or Firm* — The Law Office of Michael E. Kondoudis

(57) ABSTRACT

An assembly comprising: (a) a test tube for receiving a blood sample or a platelet-comprising fraction thereof and for obtaining therein, by a procedure that includes centrifugation, a platelet rich plasma (PRP) fraction; (b) an elongated filter device having a first and second end and a lumen extending there between, and having a filter fitted at the first end, the filter having a effective pore size such to permit passage of platelets and not permit passage of white blood cells (WBC) larger than a defined size into the lumen, the second end having an opening; the first end of the elongated filter device being adapted for tight fitting into said test tube such that when forced into the test tube to exert pressure on the PRP fraction, the PRP fraction with the platelets filters into said lumen and white blood cells of a size large than said defined size remain in the test tube to thereby obtain a WBC-selective PRP within said lumen.

22 Claims, 15 Drawing Sheets

(56) References Cited

U.S. PATENT DOCUMENTS

| | | | |
|---|---|---|---|
| 5,268,148 A * | 12/1993 | Seymour | 422/419 |
| 5,344,561 A * | 9/1994 | Pall et al. | 210/508 |
| 5,360,545 A * | 11/1994 | Pall et al. | 210/505 |
| 5,472,605 A * | 12/1995 | Zuk, Jr. | 210/436 |
| 5,501,795 A * | 3/1996 | Pall et al. | 210/508 |
| 5,587,070 A * | 12/1996 | Pall et al. | 210/202 |
| 5,651,765 A * | 7/1997 | Haworth et al. | 604/6.09 |
| 5,707,520 A * | 1/1998 | Kuroki et al. | 210/436 |
| 5,728,306 A * | 3/1998 | Breillatt et al. | 210/767 |
| 5,744,047 A * | 4/1998 | Gsell et al. | 210/767 |
| 5,951,877 A * | 9/1999 | Langley et al. | 210/782 |
| 5,998,214 A * | 12/1999 | Guirguis | 436/165 |
| 6,015,500 A * | 1/2000 | Zuk, Jr. | 210/767 |
| 6,322,709 B1 * | 11/2001 | Krasnoff et al. | 210/739 |
| 6,610,002 B2 * | 8/2003 | Dolecek | 494/37 |
| 6,692,702 B1 * | 2/2004 | Burshteyn et al. | 422/534 |
| 6,692,968 B2 * | 2/2004 | Burshteyn et al. | 436/63 |
| 6,890,728 B2 * | 5/2005 | Dolecek et al. | 435/40.5 |
| 7,413,652 B2 * | 8/2008 | Dolecek et al. | 210/380.1 |
| 7,744,820 B2 * | 6/2010 | Togawa et al. | 422/535 |
| 7,897,054 B2 * | 3/2011 | Dolecek et al. | 210/787 |
| 7,963,901 B2 * | 6/2011 | Langley et al. | 494/45 |
| 2001/0053547 A1 | 12/2001 | Slichter | |
| 2003/0209479 A1 * | 11/2003 | Lynn et al. | 210/257.1 |
| 2005/0236325 A1 * | 10/2005 | Dolecek et al. | 210/512.1 |
| 2006/0180542 A1 * | 8/2006 | Mari et al. | 210/489 |
| 2006/0278588 A1 * | 12/2006 | Woodell-May | 210/787 |
| 2007/0082370 A1 * | 4/2007 | Togawa et al. | 435/7.21 |

OTHER PUBLICATIONS

Eppley et al., Platelet Quantification and Growth Factor Analysis from Platelet-Rich Plasma: Implications for Wound Healing, Plastic and Reconstructive Surgery, Nov. 2004, pp. 1502-1508, vol. 114 No. 6, Wolters Kluwer Health/Lippincott Williams & Wilkins.

Eppley et al., Platelet-Rich Plasma: A Review of Biology and Applications in Plastic Surgery, Plastic and Reconstructive Surgery, Nov. 2006, pp. 147e-159e, vol. 118 No. 6, Wolters Kluwer Health/Lippincott Williams & Wilkins.

Kajikawa et al., Platelet-rich plasma enhances the initial mobilization of circulation-derived cells for tendon healing, Journal of Cellular Physiology, Jun. 2008, pp. 837-845, vol. 215 No. 3, John Wiley & Sons, Inc.

Otto, Skin rejuvenation and dermal filling using the body's own natural filler called Autologous Platelet Rich Plasma (PRP), Retrieved at <<http://www.theottoclinic.ie/skin_rejuvenation.htm>>, The Otto Clinic.

* cited by examiner

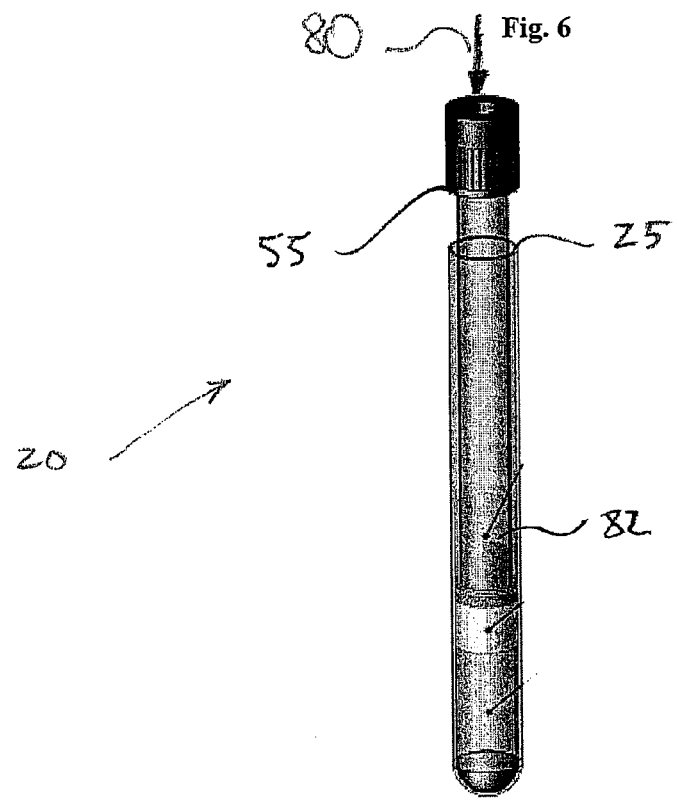
Fig. 6A
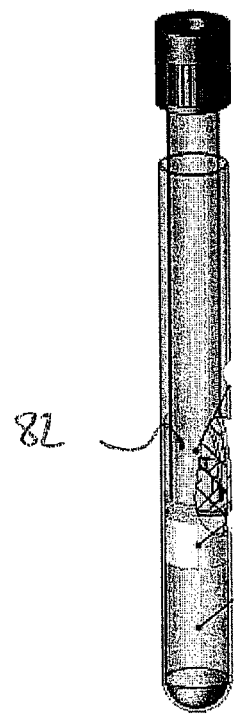

ASSEMBLY, DEVICE KIT AND METHOD FOR PREPARING PLATELET-RICH PLASMA (PRP)

FIELD OF THE INVENTION

Various embodiments of the invention relate to assemblies, devices, kits and methods for preparing a platelet-rich plasma (PRP).

BACKGROUND OF THE INVENTION

PRP is a product of blood plasma that is rich in platelets. PRP may be used in a variety of therapeutic or cosmetic applications including enhancing wound healing in dental implants and sinus elevations, heart surgery, orthopedic surgery and dermatology (chronic wound healing) [Barry L. et al, Plastic Reconstructive Surgery 114(6): pp. 1502-1508, 2004; Barry L. et al, Plastic Reconstructive Surgery 118(6): 147e-15, 2006; and Kajikawa Y. et al, J. Cell Physiol., 215(3): pp. 837-45, 2008; and Jacques Otto (published online: http://www.theottoclinic.ie/skin_rejuvenation.htm). PRP may also be utilized as a culture medium for cell expansion in the laboratory.

WO2005/065269 discloses several compositions comprising PRP and fibroblast cells for the treatment of skin, in particular, repeated administration of PRP in a dermatologically acceptable carrier to skin to e.g. reduce appearance of wrinkles.

SUMMARY OF THE INVENTION

Various exemplary embodiments of the invention are directed towards, an assemblies, devices, kits and methods to obtain PRP in a state ready for use in therapeutic or cosmetic applications or procedures. Optionally, whole blood is withdrawn from a subject, inserted into a test tube for centrifugation-based separation of the PRP fraction.

One aspect of some embodiments of the invention relates to an elongated filter device that has a filter at one end, the filter having an effective pore size such to permit passage of platelets and not permit passage of white blood cells (WBCs) larger than a defined size. The other end of the elongated filter device has an opening. Said one end fits tightly within the walls of the test tube. For obtaining PRP said one end of the elongated filter device is forced into the test tube and thereby applying pressure on the fluid content within the test tube. Fluid with the platelets then filters into the hollow tube, while the WBCs (or at least those with a size larger than said effective pore size) are filtered out. Thus, a substantially WBC-selective PRP is obtained within the hollow tube and can then be withdrawn through said other end and used within the framework of medical or cosmetic procedures. There are different types of WBCs which, among others, differ from one another in their size. It is possible, according to the invention, for the filter to have a defined effective pore size to permit passage into the elongated filter device of WBCs of certain categories smaller than its effective pore size, while filtering out other WBCs.

In accordance with one aspect of the invention, there is provided an assembly for preparing PRP comprising a test tube and an elongated filter device. The test tube is adapted for receiving whole blood and for obtaining therein, by procedures including centrifugation, a PRP fraction. Such test tubes may be, although not necessarily, of a kind known in the art.

The elongated filter device has first and second ends and a lumen that extends therein. Fitted at the first end is a filter that has an effective pore size so as to provide passage for a platelet therethrough, while not permitting passage of WBCs larger than a defined size, into the lumen. The second end of said elongated filter device is open. The first end of the elongated filter device is adapted to tightly fit into the test tube, such that when forced into the test tube, it can exert pressure on the PRP fraction to cause said fraction to filter into the lumen, through the filter, while retaining WBCs of a size larger than said defined size in the test tube.

Through such procedure, a WBC-selective PRP is obtained in the lumen, which can be withdrawn by use of a syringe which is inserted through the other end and used, e.g. even as such, for injection within the framework of a medical or cosmetic procedure. In one embodiment, the WBC-selective PRP can be allowed to clot and thereafter collected and used for a medical or a cosmetic procedure.

According to another aspect of the invention, there is provided a kit for preparing a WBC-selective PRP that comprises said assembly. Optionally, the kit includes packaging material and/or instructions for use and/or a blood withdrawal tool (e.g. needle and/or syringe). In some exemplary embodiments of the invention, kits are provided as single unit packs (i.e. sufficient components to process a single sample). In other exemplary embodiments of the invention, kits are provided as multiple unit packs (i.e. sufficient components to process multiple samples; e.g. 10; 25, 50, 100, 500 or 1000 samples or intermediate or greater numbers of samples).

By a further aspect of the invention, there is provided a method of preparing a WBC-selective PRP that comprises centrifuging a test tube containing whole blood obtained from a subject, thereby obtaining a platelet poor plasma (PPP) fraction, a platelet rich plasma (PRP) fraction and optionally a platelet pellet. The PPP fraction is then removed from the collection tube. Optionally, the platelet pellet may be suspended in the PRP. An elongated filter device is provided that has a first end fitted with a filter and a second end with an opening and a lumen therein extending between the two ends. Said filter has an effective pore size such to permit passage of platelets and not permit passage of white blood cells into the lumen, the elongated filter device being adapted for tight fitting into said test tube. Said elongated filter device forced into said test tube to, thereby exert pressure on the PRP fraction causing said fraction to pass through the filter into said lumen while the WBCs or at least a substantial portion of them that has a size larger than said effective pore size, remain in the test tube to thereby obtain a WBC-selective PRP within said lumen.

According to one embodiment of the invention, said assembly comprises a grip that can be fitted over a second end of the elongated filter device that permits the user to grip it and thereby force it into the test tube. In use, for the purpose of forcing said elongated filter device into the test tube, the test tube and the elongated filter device are axially aligned and the elongated filter device is axially forced into the test tube. Typically, but not exclusively, the grip has a leading edge formed and positioned in manner so as to limit the axial movement of said elongated filter device into the test tube.

In accordance with an embodiment of the invention, the filter has pores with a cut-off size less than 5, 7, 8, 10, 12, 14, 17, 20 or 23 µm. In accordance with an embodiment of the invention, prior to use, the platelets in the WBC-selective PRP are activated. This may be achieved, according to one embodiment, by mixing the WBC-selective PRP with an activating agent, such as thrombin and $CaCl_2$.

In another aspect, the present invention provides a second assembly for preparing platelet-rich plasma (PRP), comprising a test tube for receiving a blood sample or a platelet-comprising blood fraction and a sliding filter member disposed within the test tube. In one embodiment, the sliding filter member comprises a body, the outer walls of the body are cylindrical shaped and adapted for fluid-tight contact with the inner walls of the test tube and is slidable in an axial direction along the test tube. The body has an axial openings there-through fitted with a filter with an effective pore size such to permit passage of platelets and not permit passage of white blood cells (WBC) larger than a defined size. The filter slider member has a specific density such that during centrifugation it is forced down into said sample or fraction to separate between a platelet-comprising upper fraction from the rest of the blood or blood fraction.

In some embodiments, the specific density of the filter slider member is between about 1.03-1.08.

According to another aspect of the invention, there is provided a kit for preparing a WBC-selective PRP that comprises said device.

In another aspect, the present invention provides a method of preparing platelet rich blood fraction having a reduced white blood cell content that makes use of said second assembly. By this method blood or a platelet-comprising blood fraction is introduced into the test tube such that it is below the filter slider member. The test tube is then centrifuged to thereby obtain a blood fraction rich with platelets and having a reduced white blood cell content above the filter member.

By one embodiment the test tube has two openings at opposite ends, each fitted with a stopper and the filter slider member is a priori inside the test tube (one of the stoppers will be referred to as "bottom stopper"; the other as "top stopper"). Blood or a platelet-comprising blood fraction is introduced through the bottom stopper and following centrifugation said member migrates towards the bottom stopper separating between a PRP fraction and RBC fraction. The PRP, typically following a suspension of the platelet pellet that may form on top of said member, is withdrawn through a top stopper.

By another embodiment a test tube with a single opening is used. Blood or a platelet-comprising blood fraction is introduced through the opening and then a filter slider member is inserted, the test tube is then typically sealed and the process proceeds in a similar manner to that of the first embodiment.

In some exemplary embodiments of the invention, there is provided an assembly. The assembly includes: (a) a test tube for receiving a blood sample or a platelet-includes fraction thereof and for obtaining therein, by a procedure that includes centrifugation, a platelet rich plasma (PRP) fraction; (b) an elongated filter device having a first and second end and a lumen extending therebetween, and having a filter fitted at the first end, the filter having a effective pore size such to permit passage of platelets and not permit passage of white blood cells (WBC) larger than a defined size into the lumen, the second end having an opening; the first end of the elongated filter device being adapted for tight fitting into the test tube such that when forced into the test tube to exert pressure on the PRP fraction, the PRP fraction with the platelets filters into the lumen and white blood cells of a size large than the defined size remain in the test tube to thereby obtain a WBC-selective PRP within the lumen.

Optionally, the tight fitting is achieved by an elastomeric ring element fitted on the external wall of the first end of the elongated filter device.

Optionally, the elongated filter device has frustoconical shape with a broad first end tapering towards the second end.

Optionally, the assembly includes a grip element for fitting around external walls of the elongated filter device.

Optionally, the grip is adapted to engage with the elongated filter device and the test tube to thereby limit the forced movement of the first end of the elongated filter device into the tube.

Optionally, the assembly includes a grip fitted over the second end and having leading edge with internal diameter identical to external diameter of the elongated filter device in a mid-portion thereof between the two ends.

Optionally, the assembly has a portion at the leading end that can engage with rim of the tube to thereby limit the forced movement of the first end of the elongated filter device into the tube.

Optionally, the opening at the second end permits a syringe access for withdrawal of the WBC-selective PRP from the lumen.

Optionally, the filter includes pores having a cutoff size of no more than approximately 5 µm, 7 µm, 8 µm 10 µm 12 µm 14 µm, 17 µm, 20 µm, or 23 µm.

Optionally, the PRP is autologous PRP.

In some exemplary embodiments of the invention, there is provided a kit for preparing platelet rich plasma (PRP) having a reduced white blood cell content (WBC-selective PRP), including an assembly according as described above.

Optionally, the kit is for use in treating a subject with the WBC-selective PRP.

Optionally, the treatment is at least one selected from the group consisting of wound healing, PRP injection to the skin, cosmetic treatment, skin regeneration treatment and anti-aging treatment.

Optionally, the PRP is autologous PRP.

In some exemplary embodiments of the invention, there is provided a method of preparing platelet rich plasma (PRP) having a reduced white blood cell content (WBC-selective PRP). The method includes: (a) centrifuging a test tube containing whole blood obtained from a subject, thereby obtaining a platelet poor plasma (PPP) fraction, a platelet rich plasma (PRP) fraction and optionally a platelet pellet; (b) removing the PPP fraction from the test tube; (c) optionally, suspending the platelet pellet in the PRP; (d) providing an elongated filter device having a first end fitted with a filter and a second end with an opening and a lumen therein extending between the two ends, the filter having a effective pore size such to permit passage of platelets and not permit passage of white blood cells into the lumen, the elongated filter device being adapted for tight fitting into the test tube; and (e) forcing the elongated filter device into the test tube, thereby exerting pressure on the PRP fraction to force the fraction with the platelets to pass through the filter into the lumen while the white blood cells (WBC) remain in test tube to thereby obtain a WBC-selective PRP within the lumen.

Optionally, the method includes (f) activating the platelets the WBC-selective PRP.

Optionally, the activation includes mixing the WBC-selective PRP with an activating agent.

Optionally, step (a) further includes suspending the platelet rich plasma (PRP) phase and/or the platelet pellet.

In some exemplary embodiments of the invention, there is provided a method as described above, wherein step (a) further includes:

(a) removing the platelet poor plasma (PPP) from the test tube; and (b) suspending the platelet rich plasma (PRP) phase and/or the platelet pellet.

In some exemplary embodiments of the invention, there is provided a method of preparing platelet rich plasma (PRP) having a reduced white blood cell content, includes:

(a) centrifuging a rigid collection tube containing whole blood obtained from a subject, thereby obtaining a platelet poor plasma (PPP) phase, a platelet rich plasma (PRP) phase and optionally a platelet pellet; and (b) obtaining a WBC-selective PRP by the use of an assembly as described herein.

Optionally, the method further includes removing the platelet poor plasma (PPP) from the collection tube.

Optionally, the method further includes:

(a) removing the platelet poor plasma (PPP) from the collection tube; and (b) suspending the remaining platelet content of the collection tube.

Optionally, the method further includes activation of the obtained platelet rich plasma (PRP).

Optionally, the method further includes activating by mixing the obtained platelet rich plasma (PRP) with an activating agent selected from the group consisting of Thrombin and $CaCl_2$.

Optionally, the PRP is autologous PRP.

In some exemplary embodiments of the invention, there is provided an assembly for preparing platelet-rich plasma (PRP), including: a test tube for receiving a blood sample or a platelet-includes blood fraction; and a sliding filter member includes a body, the outer walls of the body are cylindrical shaped and adapted for fluid-tight contact with the inner walls of the test tube and slidable in an axial direction along the test tube; the body has an axial openings therethrough fitted with a filter with an effective pore size such to permit passage of platelets and not permit passage of white blood cells (WBC) larger than a defined size, the filter slider member having a specific density such so that during centrifugation it is forced down into the sample or fraction to separate between a platelet-includes upper fraction from the rest of the blood or blood fraction.

Optionally, the specific density of the slider filter member is between about 1.03-1.08.

Optionally, the test tube has openings at its two ends fitted with stoppers.

Optionally, the filter includes pores having a cutoff size of no more than approximately 5 μm, 7 μm 10 μm 12 μm 14 μm, 17 μm, 20 μm, or 23 μm.

In some exemplary embodiments of the invention, there is provided a kit for preparing platelet rich plasma (PRP) having a reduced white blood cell content (WBC-selective PRP), including an assembly as described herein.

In some exemplary embodiments of the invention, there is provided a method of preparing platelet rich plasma (PRP) having a reduced white blood cell content (WBC-selective PRP). The method includes: (a) centrifuging a test tube having a slider filter with an effective pore size such to permit passage of platelets and not permit passage of white blood cells (WBC) larger than a defined size, the test tube containing whole blood obtained from a subject, thereby obtaining a platelet poor plasma (PPP) fraction, a platelet rich plasma (PRP) fraction and optionally a platelet pellet; and (b) optionally, suspending the platelet pellet in the PRP; thereby obtaining a WBC-selective PRP.

Optionally, the method includes (c) activating the platelets the WBC-selective PRP.

In some exemplary embodiments of the invention, there is provided a method of preparing platelet rich blood fraction having a reduced white blood cell content, which includes introducing blood or a platelet-including blood fraction into an assembly as described herein and centrifuging the assembly; thereby obtaining a blood fraction rich with platelets and having a reduced white blood cell content above the filter member.

Optionally, the method further includes:

(a) removing the platelet poor plasma (PPP) from the test tube; and (b) suspending the remaining platelet content of the test tube.

Optionally, the method further includes activation of the obtained platelet rich plasma (PRP).

In some exemplary embodiments of the invention, there is provided a filtration device which includes: a sleeve with a filter in its base, the filter having a pore size which permits passage of platelets but does not permit passage of at least a selected fraction of white blood cells (WBC) and adapted to:

(i) circumferentially contact an inner wall of a test tube; and (ii) slidingly descend into the test tube in response to an applied pressure.

In some exemplary embodiments of the invention, there is provided a kit for preparing platelet rich plasma (PRP) which includes: a device as described above and the test tube.

In some exemplary embodiments of the invention, there is provided a method of preparing platelet rich plasma (PRP) which includes: (a) pre-treating a blood sample to produce a platelet poor plasma (PPP) fraction, a platelet rich plasma (PRP) fraction and, optionally, a platelet pellet; (b) removing the PPP fraction; (c) optionally, suspending the platelet pellet in the PRP; (d) in a test tube, causing a filter having a pore size which permits passage of platelets but does not permit passage of at least a selected fraction of white blood cells (WBC) circumferentially contact an inner wall of a test tube and slidingly descend into the test tube so that a WBC depleted PRP fraction accumulates above the filter.

In some exemplary embodiments of the invention, there is provided an assembly which includes: (a) a collection tube adapted to receive blood or a blood fraction including platelets; and (b) a sliding filter member adapted for fluid-tight contact with inner walls of the test tube and slidable axially into the test tube and fitted with a filter having a pore size which permits passage of platelets but does not permit passage of at least a selected fraction of white blood cells (WBC); wherein the filter member is characterized by a specific gravity selected so that during centrifugation at a defined g-force it descends into the blood or fraction to produce platelet-rich plasma (PRP) above the filter.

In some exemplary embodiments of the invention, there is provided a method which includes: (a) providing whole blood in a test tube; (b) inserting into the tube above the whole blood a sliding filter member fitted with a filter having a pore size which permits passage of platelets but does not permit passage of at least a selected fraction of white blood cells (WBC) and adapted for fluid-tight contact with inner walls of the test tube; (c) centrifuging the test tube to produce a platelet poor plasma (PPP) fraction distally above the filter, a platelet pellet in proximity to an upper surface of the filter and a platelet rich plasma (PRP) fraction between the PPP and the pellet thereby obtaining PRP having a reduced white blood cell content (WBC-selective PRP).

Optionally, the method includes re-suspending the pellet in the PRP.

The invention will now be further illustrated by description of some specific embodiments with reference to the annexed drawings. As will be appreciated, the illustrated embodiments are exemplary only of the wider scope of the invention, as described herein, and are not intended to be limiting.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 7A is a perspective view of the slider filter; FIGS. 7B and 7C show side and top view of the slider filter, respectively; and FIG. 7D is a cross-section of the slider filter.

FIG. 8A is a perspective view of the slider filter; FIGS. 8B and 8C show side and top view of the slider filter, respectively and FIG. 8D is a cross-section of the slider filter.

DETAILED DESCRIPTION OF EMBODIMENTS

The term "PRP" or "platelet rich plasma" as used herein should be understood to mean a blood product which comprises platelets concentrate in a small volume of plasma. The term "PRS" is used herein to denote a platelet rich serum.

The term "WBC-selective PRP" as used herein should be understood to encompass PRP having reduced number of white blood cells or a selective population of WBCs. The term "WBC-selective PRP" typically refers to a PRP that comprises WBCs at a concentration which is less than 50%, at times less than 40%, 30%, 20%, 10%, 5%, 4%, 3%, 2% or even less than 1% than that in the blood. The term "WBC-selective PRP" may also refer to PRP devoid of a certain population of WBCs, typically such that are filtered-out by a filter with a certain pore size.

As used herein the term "about X" or "approximately X" or "substantially X" usually refers to a range 25% less than to 25% more than of X (X±25%), at times X±20%, X±15% and preferably X±10%.

The PRP or PRS obtained in accordance with the invention may be used for treating aging skin and wrinkled-skin cells, accelerating healing of bone cells, treating surgery wounds, diabetic wounds, ulcer wounds, and pressure wounds and is used as autologous biological cells formation and/or biological glue.

In particular, some exemplary embodiments of the invention enable the preparation of PRP in a practitioner's treatment settings. The preparation of a WBC-selective PRP according to the invention is relatively rapid, e.g. about 30, 40, 50 or 60 minutes.

Figure 1A:
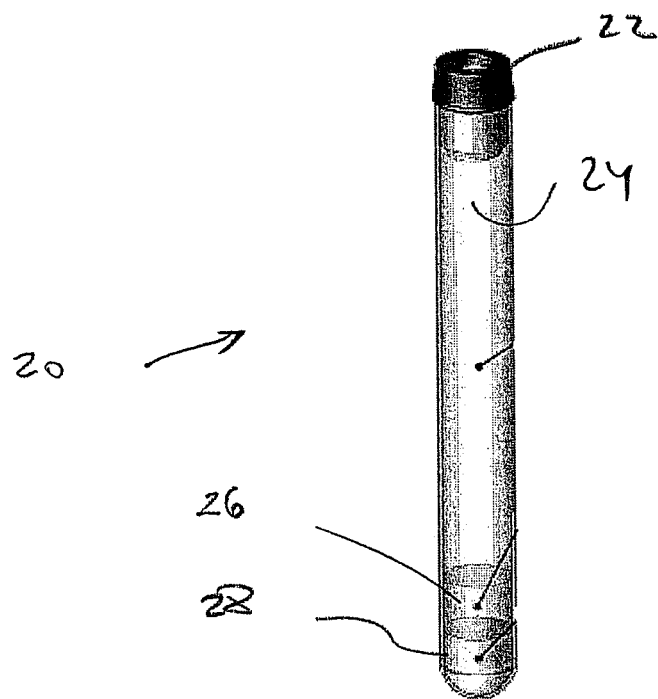
FIG. 1A shows a test tube in accordance with an embodiment of the invention.

Reference is being made to FIG. 1A showing a test tube, which is part of an assembly in accordance with the invention. The test tube 20 is provided with a stopper/closure 22, typically made of rubber, and is provided in the kit such that its interior 24 maintains a vacuum.

In some embodiments, test tubes are made of glass or MPA (modified poly Amide) or modified PET (Poly Ethylene Terephtalate). In some embodiments, the test tube has a layered structure such that the interior wall of the test tube comprises polypropylene. Test tubes can further be provided with a special stopper. By way of non-limiting example the stopper is made of butyl rubber or its halo derivative formulations at hardness between 40-60 Shore A. The hardness assures stable vacuum for at least the shelf life of the test tube which can be between 18-24 months.

The test tubes used can be of various sizes which depend of the required quantity of whole blood to be drawn from the treated subject. The test tubes have typically a size suitable for blood samples in the range of 4 ml to 100 ml.

The test tubes, by some embodiments, can contain an anti-coagulant 26 such as, but not limited to buffer citrate, modified ACD (citric/citrate dextrose), heparinate salts, EDTA salts, iodo acetate salts, oxalate salts, fluoride salts as water solutions or lyophilized material or wet or dry spray on inner wall and so forth.

While test tube may optionally include an anti-coagulant 26, in some procedures an anti-coagulant may a priori not be included. For example, if the blood sample is withdrawn and maintained in cold conditions, an anti-coagulant may not be needed. In addition, in some procedures, the anti-coagulant may be mixed with the whole blood which was withdrawn from a subject, prior to inserting the whole blood into the tube.

In some embodiments, test tubes contain a barrier-forming substance 28 to assist in the centrifugation-based separation of blood into its components. Such barrier-forming substance may be of the kind known per se, for example gel polymers. Gel polymers may, for example, be based on polyacrylic, polyolefin or polyester with a specific gravity in the range of about 1.03 to 1.08 (e.g. 105). Following centrifugation, blood components, particularly red blood cells, will remain beneath the gel barrier and other, including platelets, will remain above it.

In some embodiments, the test tubes or the kit will contain an activator such as, but not limited to thrombin, silicate based formulations or $CaCl_2$. In cases where chemically induced activation is not desired, activation can be affected by mechanical means known in the art, including the use of test tubes having specialized clot nucleation sites. Examples are polystyrene and/or glass beads and microbeads that can serve as blood clot accelerator (BCA)

Figure 1B:
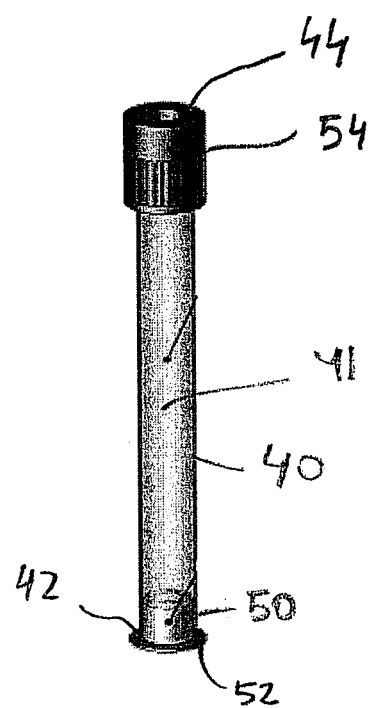
FIG. 1B shows a hollow tube in accordance with an embodiment of the invention.
Figure 1C:
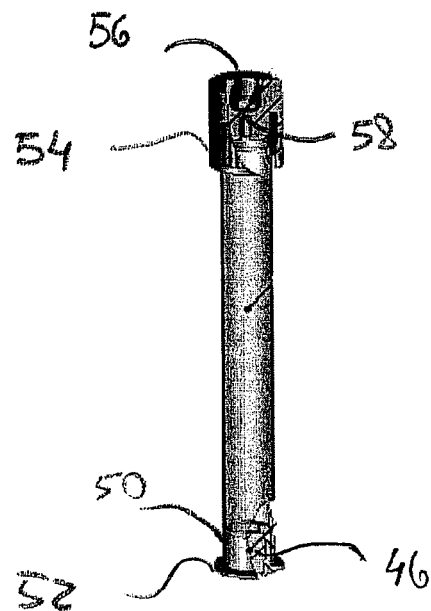
FIGS. 1C and 1D show said elongated filter device of FIG. 1B with a portion of the exterior cut off to show the internal structure (FIG. 1C) and in cross-section (FIG. 1D).
Figure 1D:
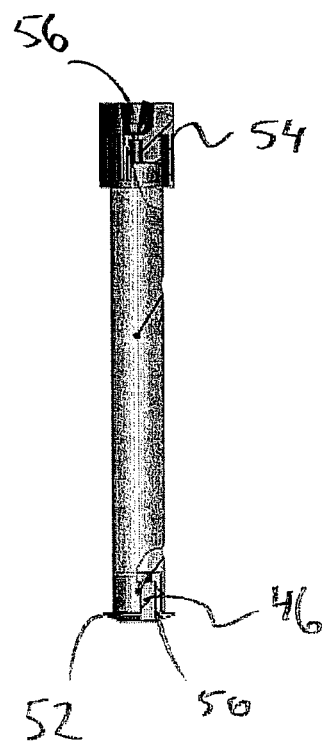

The assembly also comprises an elongated hollow tube 40 shown in FIG. 1B. Tube 40 is sometimes referred to as a "sleeve" in the specification, examples and claims. The hollow tube 40 has a lumen 41 that extends between a first end 42 and a second end 44. The first end, or base, is fitted with a filter 46, which is detailed in FIGS. 1C and 1D. The filter has an effective pore size that permits passage of platelets but blocks passage therethrough of larger cellular material. Platelets typically have a size in the range of 2-4 μm and the effective pore size may typically be such to permit passage of platelets but not permit passage of WBCs which have a size larger than approximately 4 μm. However, at times, the effective pore size may be such to permit passage of certain smaller WBCs, while blocking larger ones. Smaller WBCs include lymphocytes such as T-cells or B-cells characterized by size distribution of 6-8 μm; larger WBCs include granulocytes and macrophages. The size of granulocytes varies according to their respective type. Neutrophils and eosinophils are characterized by a size distribution of about 10-12 μm, while basophils are characterized by a size distribution of about 10-15 μm.

Additionally, the size of a macrophage is about 21 μm. Monocytes are characterized by a size distribution of about 14-17 μm. The chosen filter with the defined effective pore size can thus enable collection, for example, of PRP together with monocytes, and lymphocytes, and exclude others. Different effective pore size can allow other combinations. For example, for those applications where granulocytes and macrophages are desired, the effective pore size will be about 25 μm.

Filter 42 is mounted on an insert 50, fitted snuggly within said first end and having a flexible skirt 52. Therefore, once end 42 is axially inserted into the test tube, the flexible skirt 52 provides a tight seal with the internal walls of the test tube. In other words, skirt 52 circumferentially contacts an inner wall of a test tube into which it is inserted. The flexible skirt 52 can be made of rubber or a ring shaped elastomer.

The second end 44 has an opening such as opening 58. Included in this embodiment is a grip member 54 fitted tightly about second end 44. The grip member 54 is formed with a central depression 56 and opening 58 that leads into lumen 41. The lumen 41 is formed, by this embodiment, within this depression. The pressure in the hollow tube's interior is thus equated with the external pressure. Furthermore, opening 58 permits the insertion of a syringe to withdraw the filtered product, i.e. the WBC-selective PRP.

Figure 2:
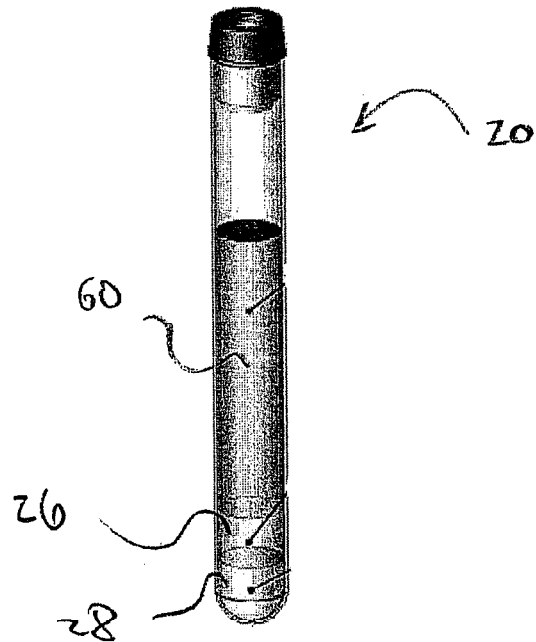
FIGS. 2-6 show successive steps of preparing WBC-selective PRP by the use of test tube and elongated filter device of FIGS. 1A and 1B.

FIG. 2 schematically illustrates a procedure for preparing WBC-selective PRP in accordance with one embodiment of the present invention. In a first step of the procedure, whole blood sample 60 withdrawn from a subject is inserted into the test tube. In some embodiments collected blood may be distributed in more than 1, e.g. two-four, blood-collection test tubes. For example, 20 ml of blood may be collected into two test tubes holding, each, 10 ml.

Through agitation/mixing, it can then mix with the anti-coagulant 26, optionally included within the test tube. Alternatively, as already noted above, the blood sample may be mixed with an anti-coagulant, prior to insertion into tube 20.

The test tube is then subjected to centrifugation. Centrifugation is used to separate the red blood cells (RBC) from the plasma and the platelets.

Centrifugation may, for example, be at about 1,000-1,500 g and for a time period of 5-10 minutes. Centrifugation results in platelet enrichment 2-5 times compared to their native concentration in whole blood.

Figure 3:
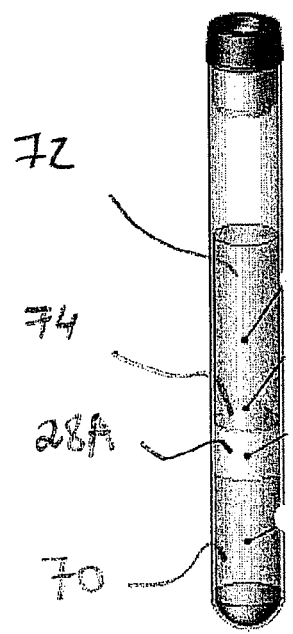

An example of such fractionated blood is shown in FIG. 3, in which the gel barrier 28A separates between the RBC fraction 70 and a plasma fraction 72.

Figure 4:
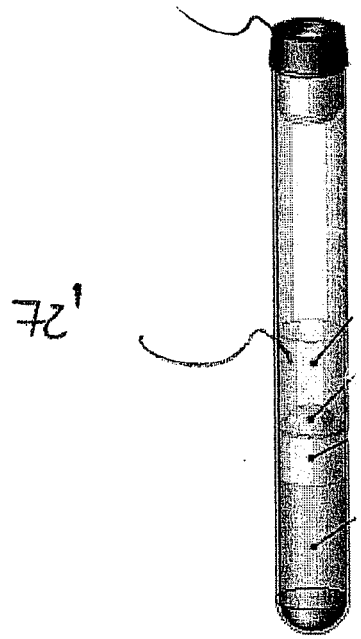
Figure 5:
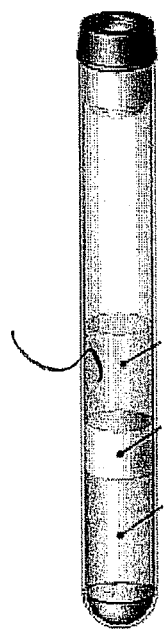

The platelets are concentrated at the bottom end of the plasma fraction, typically forming a pellet 74. By removal of part of the plasma to yield more enriched plasma 72' which is shown in FIG. 4 and by subsequent agitation, a PRP fraction 76 is obtained, as shown in FIG. 5.

Figure 6B:
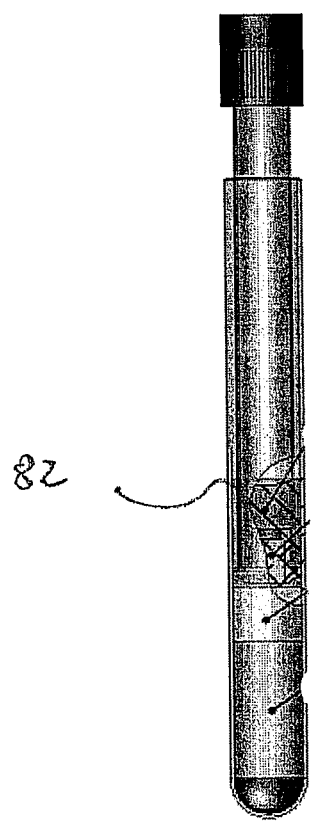
Figure 7A:
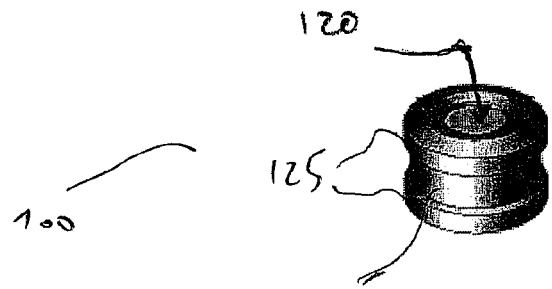
FIGS. 7A-7D is an illustration of a slider filter in accordance with an embodiment of the invention.
Figure 7B:
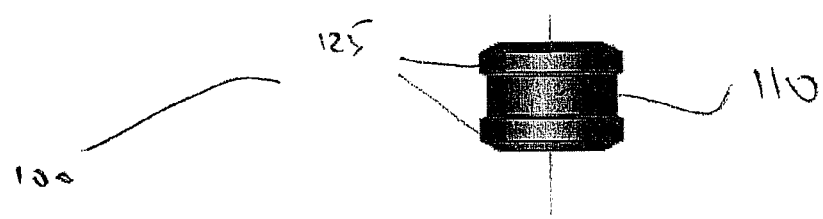
Figure 7C:
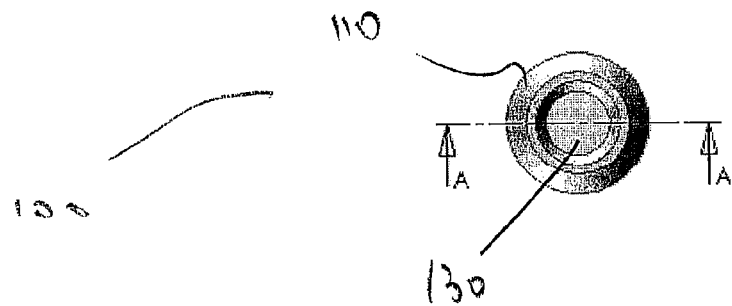
Figure 7D:
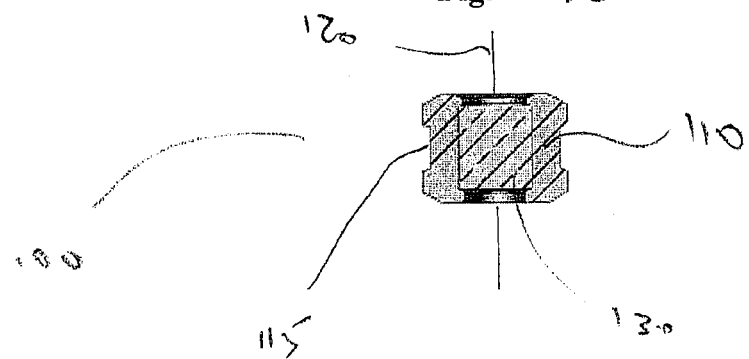
Figure 8A:
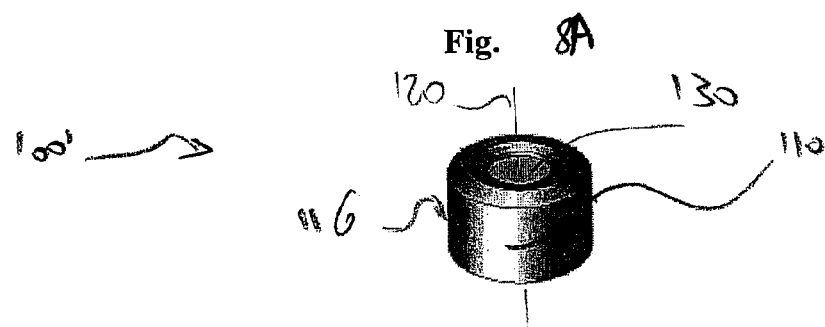
FIGS. 8A-8D is an illustration of a slider filter in accordance with an embodiment of the invention.
Figure 8B:
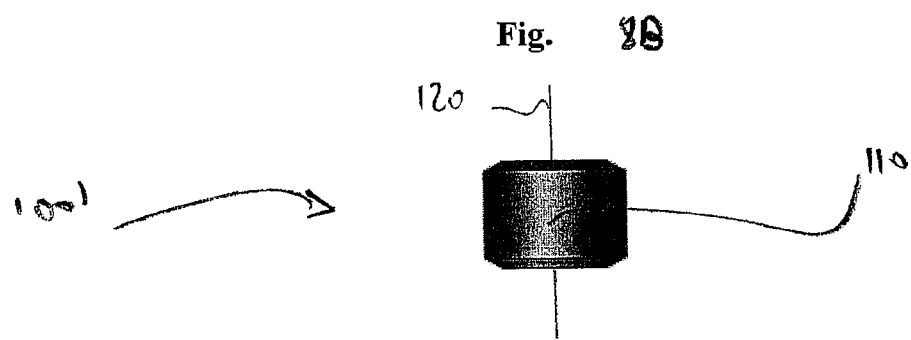
Figure 8C:
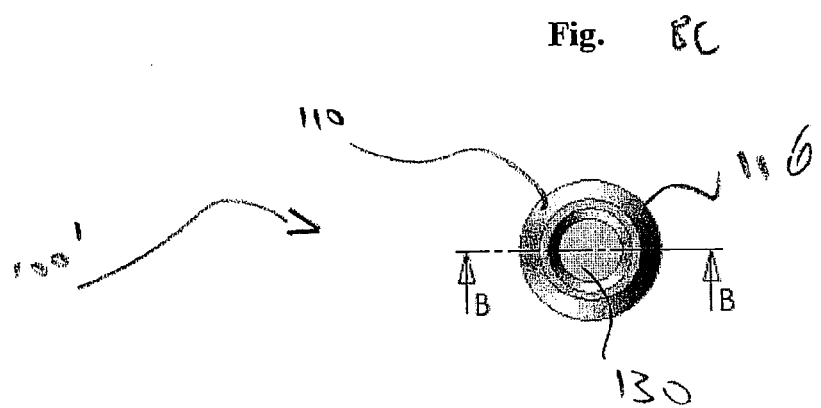
Figure 8D:
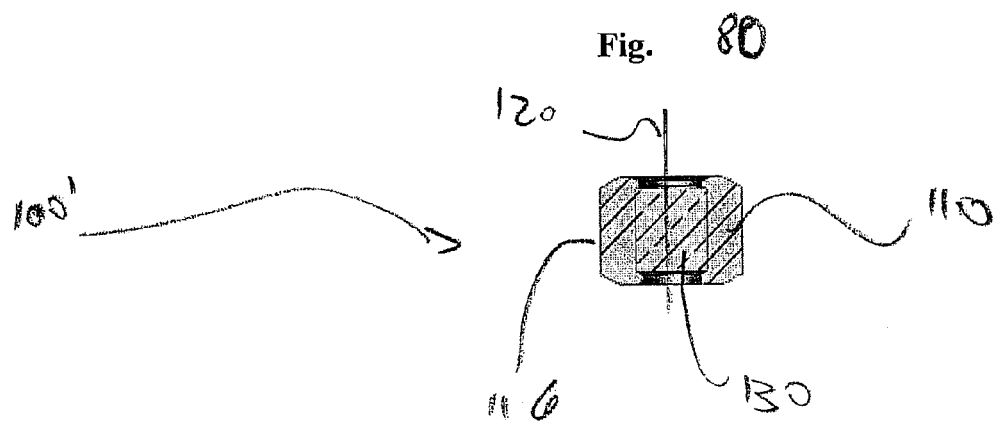

At this stage, the stopper 22 is removed, and hollow tube 40 is then inserted by axially aligning the two and axially forcing the latter into the former, in the direction of arrow 80 shown in FIG. 6. This exerts pressure on the PRP fraction 76 to thereby force the PRP with the platelets into the lumen 41 through the filter 46 to thereby obtain a WBC-selective PRP 82 in said lumen, as can also be seen in FIGS. 6A and 6B.

In some embodiments of the invention, leading edge 55 of the grip member 54 is so configured and positioned so as to provide a limit for the axial movement of elongated filter device 40 into test tube; namely this axial movement will proceed until said edge comes into contact with the lips 25 of the test tube 20. In other words leading edge 55 of grip member 54 limits sliding descent of elongated filter device 40 into the test tube in response to an applied pressure. By use of a suitable needle, the WBC-selective PRP 82 can then be withdrawn into a syringe and subsequently used within the framework of a medical or a cosmetic procedure.

The kit in accordance with the invention typically includes, at the minimum, a test tube, such as test tube 20, and an elongated filter device, such as elongated filter device 40. Additionally, a kit may also include a variety of reagents such as clotting activators, and anticoagulants, a syringe for withdrawal of blood from the patient, as well as a syringe with a needle adapted for withdrawal of the WBC-selective PRP from the elongated filter device and subsequent inoculation of a subject.

In accordance with some embodiments provided in the kit, the PRP may be activated by reagents such as thrombin and calcium dichloride which may be inoculated into the lumen of said hollow tube, prior to withdrawal of the WBC-selective PRP or may be retained within the syringe and mixed with the WBC-selective PRP following its withdrawal into the syringe.

Figure 9:
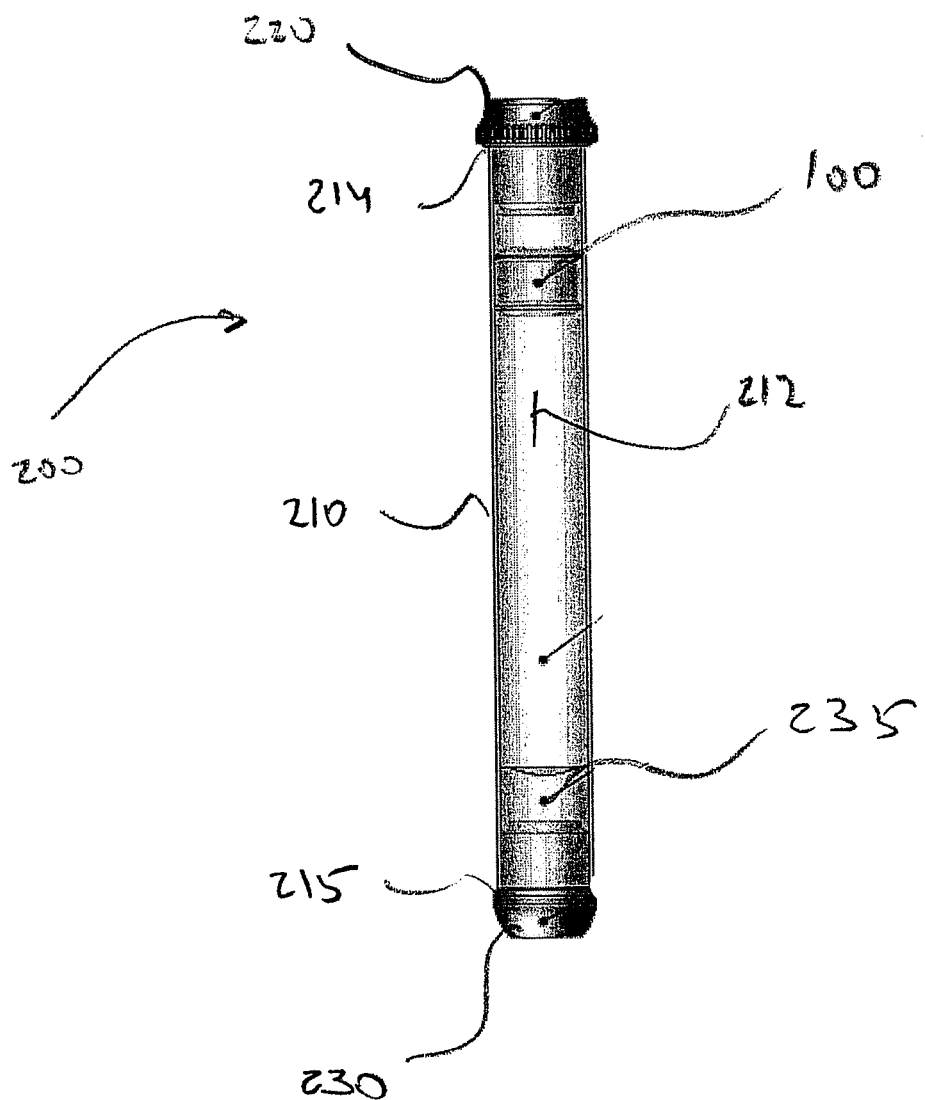
FIG. 9 shows an assembly of a test tube and a slider filter member in accordance with an embodiment of the invention.

Reference is first being made to FIG. 9 showing a side view of an assembly in accordance with an embodiment of said second assembly of the invention. The assembly 200 comprises a test tube 210 for receiving a blood sample or a platelet-comprising blood fraction. The test tube 210 has a lumen 212 that extends between a first end 214 and a second end 215, fitted, respectively with stoppers 220 and 230. The stoppers 220 and 230 are typically made of rubber or another elastomeric material. The top and bottom stoppers 220 and 230 have a central portion (not shown) that may be pierced by a needle for introducing or withdrawal of liquids to and from the lumen 212.

Typically, the test tube's interior maintains a vacuum. The test tubes, by some embodiments, can contain an anticoagulant 235, such as those noted above.

The assembly 200 comprises a slider filter member 100, which is shown in more details in FIGS. 7A-7D. The slider filter member has a body 110 with a cylindrical middle portion 115 flanked by two annularly abutting portions 125. Portions 125 have a diameter such that they fit snuggly within the inner walls of test tube 210, to thereby form a fluid-tight contact therewith. In some embodiments, the body 110 or at least the annular abutments 125 are made of a resilient material.

The slider filter is slidable in an axial direction along the test tube. The body 110 has an axial opening 120 therethrough fitted with a filter 130. The filter 130 has an effective pore size such to permit passage of platelets and not permit passage of white blood cells (WBC) larger than a defined size. Regarding pore size determine criteria—see above.

Another embodiment of a slider filter member 100' is shown in FIG. 8A-8D. The slider filter member 100' is similar to the embodiment illustrated in FIG. 7A-7D and like element are indicated with like reference numerals. In this case body 110 has cylindrical outer wall 116 with a diameter to fit snugly within the inner walls of test tube 210 to thereby form a fluid-tight contact therewith.

In some embodiments, the specific density of the filter slider member 100 ranges between about 1.03 to 1.08. The density allows centrifugal separation of blood fractions in accordance with their respective densities in conjunction with filtration of WBCs, in a manner to be explained further below.

Figure 10:
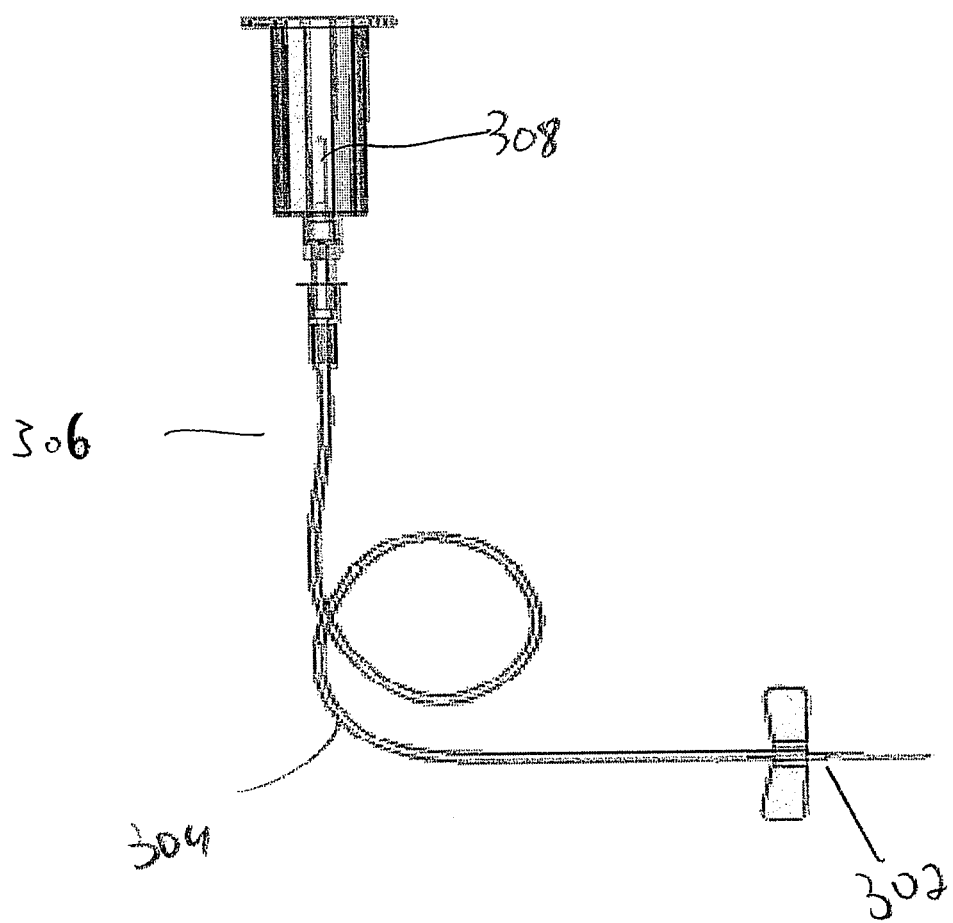
FIG. 10 shows a blood drawing kit comprising of a blood drawing assembly, holder attached to Luer adapter attached to butterfly needle for use in conjunction with the assembly of FIG. 9.

FIGS. 11A-11F illustrate a procedure for preparing WBC-selective PRP utilizing the test tube of FIG. 9. Whole blood sample can be drawn from a subject by using a blood drawing device 300 shown in FIG. 10, known per se having a vein needle 302, a flexible tube 304 and test tube adapter 306 with a piercing member 308 (Holder attached to Luer adapter attached to PSV Butterfly).

Figure 11A:
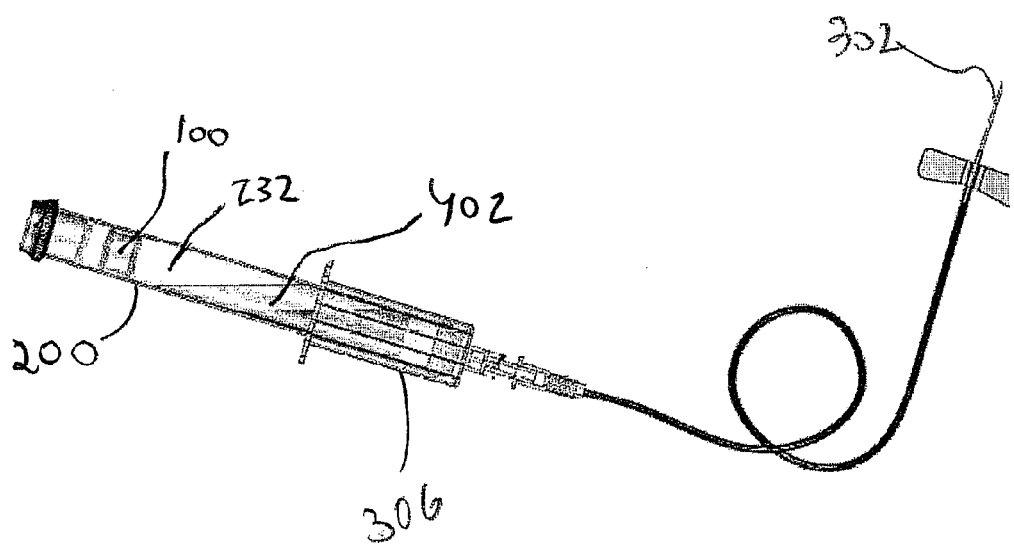
FIGS. 11A-11F show successive steps of preparing WBC-selective PRP by the use of an assembly of a test tube and slider filter device of FIGS. 8A and 8D in accordance with an embodiment of the invention.
Figure 11B:
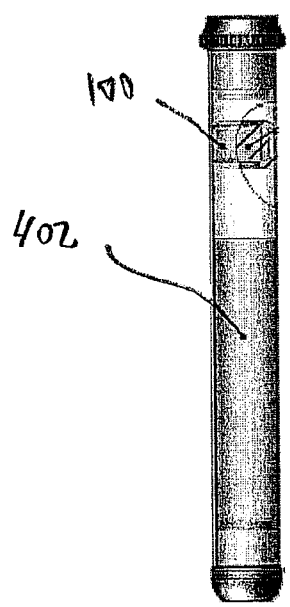

In use, needle 302 is inserted into a vein, and upon connecting the test tube to adapter 306, as can be seen in FIG. 11A, member 308 pierces the central portion of the bottom stopper 230 and as a consequence of the vacuum inside the test tube, blood 402 is withdrawn thereinto. Anti-coagulant 235, optionally included within the test tube, becomes mixed with the blood sample inhibiting clotting. Eventually, after disconnecting the tube from the blood drawing device, a test tube with a blood sample 402, optionally mixed with an anti-coagulant, and a filter slider member above it is obtained as shown in FIG. 11B.

Figure 11C:
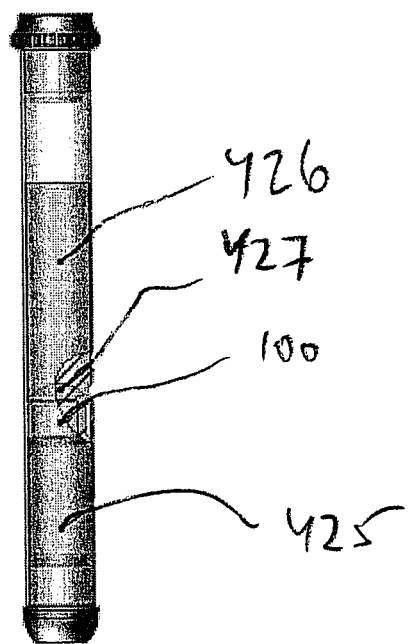
Figure 11D:
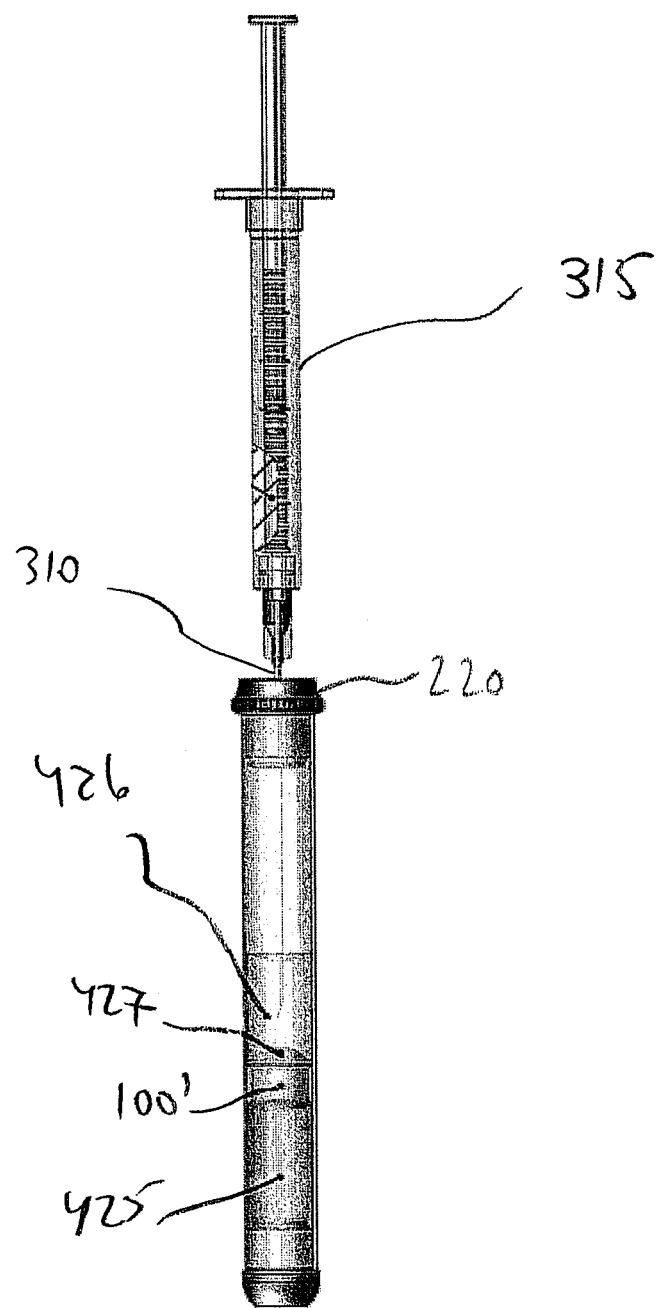
Figure 11E:
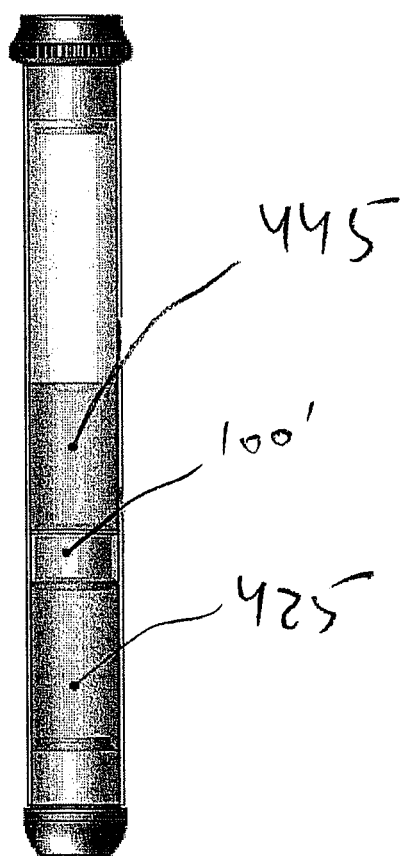
Figure 11F:
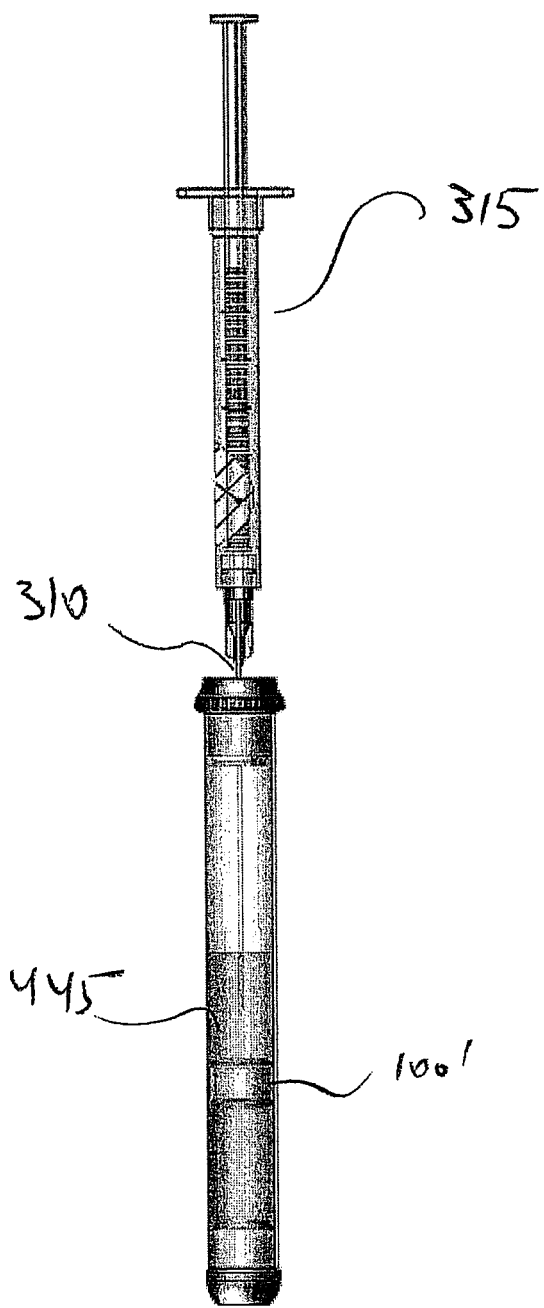

The test tube is then subjected to centrifugation. During the centrifugation procedure the filter slider member 100 is forced down into the blood sample thereby eventually separating between a PRP fraction 426 and an RBC-comprising fraction 425, as shown in FIG. 11C. Depending on the pore size, the PRP fraction may contain also some WBCs. A Platelet pellet 427 typically forms on top of the filter member 100, which may be suspended in the PRP in a subsequent step. Centrifugation may be at about 400-800 g and for a time period of 5-15 minutes. The platelet content of the PRP 426 in enriched about 2-5 times more in comparison to their native concentration in whole blood. The PRP 426 may then be withdrawn with a syringe 315 through via a needled inserted through the pierceable portion of stopper 220.

In some embodiments, the RBC fraction may be removed with a syringe via a needled inserted through pierceable portion of bottom stopper 230, followed by a second, more rigorous centrifugation step, for example 1,000-1,500 g and for a time period of 5-15 minutes. The second centrifugation will usually yield a more pronounced platelet pellet 427 on top of the slider filter 100.

Additionally, the PRP or autologous PRP prepared in accordance with some exemplary embodiments of the invention can also be injected as a mesotherapy technique. The later typically comprises multiple superficial injections into the skin. The PRP can further optionally be used like synthetic dermal filler applied into wrinkles, lines and for use in lip-, cheek-, and chin augmentation. The duration of such rejuvenation process is approximately 300 days, but the clinical effect can last longer because of new collagen and elastin formation.

It is expected that during the life of this patent many gel types and/or filter media will be developed and the scope of the invention is intended to include all such new technologies a priori.

As used herein the term "about" refers to ±10%.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Specifically, a variety of numerical indicators have been utilized. It should be understood that these numerical indicators could vary even further based upon a variety of engineering principles, materials, intended use and designs incorporated into the invention. Additionally, components and/or actions ascribed to exemplary embodiments of the invention and depicted as a single unit may be divided into subunits. Conversely, components and/or actions ascribed to exemplary embodiments of the invention and depicted as sub-units/individual actions may be combined into a single unit/action with the described/depicted function.

Alternatively, or additionally, features used to describe a method can be used to characterize an apparatus, assembly or kit and features used to describe an apparatus, assembly or kit can be used to characterize a method.

It should be further understood that the individual features described hereinabove can be combined in all possible combinations and sub-combinations to produce additional embodiments of the invention. The textual description, figures and examples presented here are illustrative in nature and are not intended to limit the scope of the invention which is defined solely by the following claims. Specifically, the invention has been described in the context of filter sleeves which slidingly descend into tubes but might also be embodied by filter sleeves which remain stationary while tubes containing a sample are raised with respect to them.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms "include", and "have" and their conjugates as used herein mean "including but not necessarily limited to".

Additional objects, advantages, and novel features of various embodiments of the invention will become apparent to one ordinarily skilled in the art upon examination of the following examples, which are not intended to be limiting. Additionally, each of the various embodiments and aspects of the invention as delineated hereinabove and as claimed in the claims section below finds experimental support in the following examples.

EXAMPLES

Reference is now made to the following examples, which together with the above descriptions; illustrate the invention in a non limiting fashion.

Example 1

Using an assembly for preparing platelet-rich plasma (PRP) of the kind shown in FIGS. 1A-1D, WBC-selective PRP can be obtained by the following procedure:

(1) Blood is drawn according to the volume dictated by the test tube, for example 20 ml of venous blood divided into 2 test tubes of 10 ml each. The test tubes include a barrier-forming gel. The test tube holds a vacuum and is closed by a closure/stopper, e.g. made of rubber.

(2) The whole blood is mixed gently in the test tube to create good contact with the anticoagulant.

(3) The test tube with the mixture is centrifuged for 5-15 minutes at about 700-1100 g or 1000-1500 g By way of non-limiting example the mixture can be centrifuged for a period of 7, 8, 10, 12, 15 minutes. Centrifugation can be performed, for example, at 700 g, 800 g, 1000 g, 1200 g or 1350 g. A gel barrier is formed separating between a fraction that includes the red-blood cell and plasma. The platelets and the WBCs have specific gravity lower than the gel, and therefore are located above the gel.

(4) PPP (Platelet Poor Plasma) is removed by a decantation method. The decantation is optionally done using a transfer pipette or a blunt needle attached to syringe. Typically, more than half of the plasma is PPP; therefore removal of more than half of the upper phase in the test tube is required.

(5) The remaining plasma above the gel barrier is vibrated to suspend the platelet pellet. This is done by vortex or another agitator type.

(6) An elongated filter device of the kind specified herein, is pushed gently in an axial direction into the test tube so that the filter at its first, leading edge passes gently through the PRP phase until the lower end of the filter is in close proximity to the upper face of the gel. Consequently a WBC-selective PRP accumulates within the lumen of said member. Depending on the effective pore size, some fraction of the WBCs, typically mononuclear cells may also enter said lumen.

(7) The elongated filter device has an opening at its second end and through this opening the WBC-selective PRP is withdrawn by a syringe with an attached needle which may be either pre-washed or un-washed with activator such as Thrombin, $CaCl_2$ solution, or silicate solution/suspension.

Results obtained by the above procedure are shown in the Table 1 below (8 minutes centrifugation at 1350 g).

TABLE 1

Platelet and WBC counts

| | | Sample number | | | | | | | | |
|---|---|---|---|---|---|---|---|---|---|---|
| | Avg | 1 | 2 | 3 | 4 | 5 | 6 | 7 | 8 | 9 |
| Name initials | | AE | TE | LT | RM | DK | YL | HU | JK | MR |
| age | | 61 | 48 | 48 | 41 | 60 | 60 | 57 | 60 | 56 |
| gender | | M | F | F | M | M | M | M | M | M |
| Whole Blood PLT count (K/μl) | 203.11 | 205 | 339 | 269 | 112 | 165 | 205 | 155 | 227 | 151 |
| whole blood volume (ml) | 11.88 | 11.5 | 12 | 11.5 | 11.5 | 12.2 | 12 | 12.4 | 11.8 | 12 |
| WBC in Whole Blood (K/μl) | 2.53 | 4.2 | 3 | 3.9 | 2.8 | 2.1 | 1.6 | 1.7 | 2.5 | 1 |
| whole blood-Total PLT | 2410.29 | 2357.5 | 4068 | 3093.5 | 1288 | 2013 | 2460 | 1922 | 2678.6 | 1812 |
| WBC in PPP (K/μl) | 0.10 | 0.1 | 0.1 | 0.1 | 0.1 | 0.1 | 0.1 | 0.2 | 0.1 | 0.1 |
| PPP: PLT count (K/μl) (D) | 61.11 | 72 | 150 | 69 | 29 | 38 | 59 | 34 | 59 | 40 |
| PPP volume (ml) | 4.00 | 4 | 4 | 4 | 4 | 4 | 4 | 4 | 4 | 4 |
| PPP: PLT-Total (K/μl) | 244.44 | 288 | 600 | 276 | 116 | 152 | 236 | 136 | 236 | 160 |
| WBC in PRP (K/μl) | 3.28 | 4.2 | 3 | 3.9 | 2.8 | 2.1 | 1.6 | 8.4 | 2.5 | 1 |
| PRP: PLT count (K/μl) | 524.78 | 582 | 733 | 819 | 277 | 370 | 503 | 535 | 562 | 342 |
| PRP volume (ml) | 3.32 | 2.8 | 4 | 3.1 | 3.5 | 3.7 | 3.5 | 2.5 | 3.4 | 3.4 |
| PRP: PLT-Total | 1734.51 | 1630 | 2932 | 2539 | 970 | 1369 | 1761 | 1338 | 1911 | 1163 |
| Total PLT(PPP + PRP) | 1978.96 | 1918 | 3532 | 2815 | 1086 | 1521 | 1997 | 1474 | 2147 | 1323 |
| PPP + PRP = % Recovery | 81.11 | 81.34 | 86.82 | 90.99 | 84.28 | 75.56 | 81.16 | 76.66 | 80.15 | 73.00 |
| PRP = % Recovery | 71.47 | 69.12 | 72.07 | 82.07 | 75.27 | 68.01 | 71.57 | 69.59 | 71.34 | 64.17 |
| PRP PLT Concentration (folds) | 2.60 | 2.84 | 2.16 | 3.04 | 2.47 | 2.24 | 2.45 | 3.45 | 2.48 | 2.26 |

F—female;
M—male;
PLT—platelet count

Example 2

An assembly of the kind shown in FIGS. 1A-1D, however without a barrier-forming gel in the test tube may also be used. In this case a gentler centrifugation at 400-800 g for 5-15 minutes may be used to get RBC in the bottom of the tube and plasma with platelet above the RBCs. The whole plasma is then decanted and transferred to another test tube which is centrifuged at 1,000-1,500 g to get pellet and PRP+WBC in the bottom and PPP at the top, the PPP is decanted and the pellet together with small portion of the PRP is agitated to get PRP+WBC at low volume of plasma. Filter sleeves with the effective desired pore size is inserted to collect the PRP with the appropriated fraction of WBC. This part is decanted to prefilled syringe with activator for further clinical use.

Results obtained by the above procedure are shown in Tables 2 and 3.

TABLE 2

| G force | 1000 | 700 | 400 | 200 | 100 |
|---|---|---|---|---|---|
| RPM (R = 10 cm) | 3000 | 2500 | 1800 | 1200 | 1000 |
| Whole blood volume (ml) | 8.5 | 8.5 | 8.5 | 8.5 | 8.5 |
| Plasma volume (ml) | 4.9 | 4.7 | 4.1 | 2.95 | 2.5 |
| Est. PPP volume (ml) | 2.45 | 2.35 | 2.05 | 1.475 | 1.25 |
| Est. PRP volume (ml) | 2.45 | 2.35 | 2.05 | 1.475 | 1.25 |
| RBC volume (ml) | 3.6 | 3.8 | 4.4 | 5.55 | 6 |
| PLT count in Whole blood (K/ul) | 184 | 184 | 184 | 184 | 184 |
| Total number of PLT in whole blood(K/ul) | 1564 | 1564 | 1564 | 1564 | 1564 |
| PLT count in PPP phase (K/ul) | 95 | 245 | 368 | 387 | 364 |
| PLT count in PRP phase (K/ul) | 263 | 380 | 363 | 383 | 378 |
| Total PLT count in PPP | 232.75 | 575.75 | 754.4 | 570.825 | 455 |
| Total PLT count in PRP | 644.35 | 893 | 744.15 | 564.925 | 472.5 |
| Total PLT count in PPP + PRP | 877.1 | 1468.75 | 1498.55 | 1135.75 | 927.5 |
| Percentage recovery after spin | 56.08% | 93.91% | 95.82% | 72.62% | 59.30% |
| PLT count after filtration (K/ul) | | 294 | 374 | | |
| Total PLT count in filtered plasma | | 1381.80 | 1533.40 | | |
| Percentage recovery after filtration | | 94.08% | 102.33% | | |
| Lymph in PPP phase (K/ul) | 0.03 | 0.25 | 1.82 | 1.45 | 2.95 |
| Lymph in PRP phase (K/ul) | 0.32 | 2.42 | 3.33 | 4.45 | 5.95 |
| Lymph in plasma after filtration (K/ul) | | 0.46 | 2.52 | | |

TABLE 3

| | G force | | | | | | | | | |
|---|---|---|---|---|---|---|---|---|---|---|
| | 670 | ## | ## | 670 | 670 | 670 | 670 | 670 | 100 | 100 |
| | Sample # | | | | | | | | | |
| | #1-1 7' spin | #1-2 7'spin | #1-2 10' spin | #1-3 7' spin | #2-1 7' spin | #2-2 7'spin | #2-2 10' spin | #2-3 7' spin | #1 10' spin | #2 10' spin |
| blood volume (ml) | 8.5 | 8.5 | 8.5 | 8.5 | 8.5 | 8.5 | 8.5 | 8.5 | 8.5 | 8.5 |
| Plasma volume (ml) | 4.3 | 4.2 | 4.2 | 4.7 | 4 | 4.2 | 4.2 | 4.3 | 2 | 1.5 |
| Est. PPP volume (ml) | 2 | | 2 | | 2 | | 2 | | | |
| Est. PRP volume (ml) | 2.3 | | 2.2 | | 2 | | 2.2 | | | |
| PLT in whole plasma/ml | | 309 | 260 | 270 | | 401 | 414 | 430 | 368 | 421 |
| PLT in whole plasma | | | 1269 | | | 1684 | 1739 | 1849 | 736 | 631.5 |
| PLT count in Whole blood (K/ul) | 156 | 156 | 156 | 156 | 203 | 203 | 203 | 203 | 156 | 203 |
| Total number of PLT in whole blood(K/ul) | 1326 | ### | ### | 1326 | 1726 | 1726 | 1726 | 1726 | 1326 | 1725 |
| PLT count in PPP phase (K/ul) | 229 | | 111 | | 383 | | 146 | 146 | | |
| PLT count in PRP phase (K/ul) | 280 | | 391 | | 406 | | 616 | 616 | | |
| Total PLT count in PPP | 458 | | 222 | | 766 | | 292 | | | |
| Total PLT count in PRP | 644 | | 860 | | 812 | | 1355 | | | |
| Total PLT count in PPP + PRP | 1102 | | 1269 | | 1578 | | 1647 | | | |
| Percentage recovery | | | | | | | | | | 36.61% |

Example 3

An assembly with a pre-inserted slider filter of the kind shown in FIG. 9 may also be used.

1) Blood is drawn into the assembly from the bottom cap of the tube. Blood is drawn according to the volume dictated by the test tube, for example 20 ml of venous blood divided into 2 test tubes of 10 ml each. The test tube holds a vacuum and is closed by a top cap and bottom cap e.g. made of rubber.

2) The whole blood is mixed gently in the test tube to create good contact with the anticoagulant.

3) The test tube with the mixture is centrifuged for 5-15 minutes at about 400-800 g. By way of non-limiting example the mixture can be centrifuged for a period of 7, 8, 10, 12, 15 minutes. Centrifugation can be performed, for example, at 700 g or 800 g. A pre-inserted slider filter separates between a fraction that includes the red-blood cell and plasma. The platelets have specific gravity lower than the slider filter, and therefore are located above the slider filter. WBCs fractions are located in accordance to their respective density and the effective pore size of the slider filter. Optionally, the RBCs fraction below the slider filter can be removed by decantation via the bottom cap. Additional centrifugation can be used to form a platelet pellet on top of the slider filter at about 1,000-1,500 g for 5-15 minutes. Other centrifugation forces may also be used as mentioned above in Example 1.

4) PPP (Platelet Poor Plasma) is removed by a decantation method. The decantation is optionally done using a transfer pipette or a blunt needle attached to syringe. Typically, more than half of the plasma is PPP; therefore removal of more than half of the upper phase in the test tube is required.

5) The remaining WBC-selective PRP above the slider filter is vibrated to suspend the platelet pellet. This is done by vortex or another agitator type.

6) WBC-selective PRP is withdrawn by a syringe with an attached needle which may be either pre-washed or un-washed with activator such as Thrombin, $CaCl_2$ solution, or silicate solution/suspension.

Example 4

Blood sample analysis was conducted in the Sheba Medical Center at Tel Hashomer, Israel. Using an assembly for preparing platelet-rich plasma (PRP) of the kind shown in FIGS. 1A-1D, WBC-selective PRP was obtained as follows. 10 ml of whole Blood was drawn from 12 individuals into tubes containing anticoagulant. The test tubes used to draw the blood included a barrier-forming gel holding a vacuum. The whole blood obtained was mixed in the test tubes. Then, the test tubes containing the mixture were centrifuged for about 8 minutes at 1350 g. More than half of the plasma was removed by decantation to deplete platelet poor plasma. The remaining plasma above the gel barrier was vibrated to suspend the platelet pellet. A filter sleeve comprises pores having a cutoff size of 10 microns (elongated filter device) was pushed in an axial direction into the test tubes to filter their content. Filtration was performed with respect to patients 1, 2, 3, 4, 6, 9 and 11. WBC-selective PRP accumulated within the lumen of the sleeve and was withdrawn by a syringe with an attached needle. The syringe contained thrombin as an activator.

Results obtained by the above procedure are shown in the Table 4. Content analysis of processed samples was preformed both immediately (t=0) following WBC-selective PRP collection and after 4 hours (t=4). It should be noted that content of the processed samples, can be obtained at t=0, t=1, t=2, t=3, t=4, t=5 or more (t, hours), at the discretion of the physician or technician employed to perform the procedure according to various embodiments of the invention.

The blood sample analysis demonstrated the WBC-selectivity of PRP preparation achievable by the assemblies, kits and of various exemplary embodiments of the invention i.e. the ability of the methods, kits and assemblies to obtain a substantially or entirely WBC-selective PRP. In particular, an assembly for preparation of PRP according to exemplary embodiments of the invention can be used to reduce the WBC content in the prepared PRP by at least a fold, 2 fold or more.

TABLE 4

| | Sample number | | | | | | | | |
|---|---|---|---|---|---|---|---|---|---|
| | 1 | 2 | 3 | 4 | 5 | 6 | 7 | 8 | 9 |
| Name initials | DK | GB | OY | DE | MB | AS | NM | DK | RL |
| age | 27 | 36 | 35 | 34 | 26 | 36 | 23 | 30 | 60 |
| gender | F | M | F | M | F | F | M | M | F |
| weight | 65 | 80 | 70 | 78 | 55 | 59 | 82 | 78 | 55 |
| medications | none | none | none | none | none | none | none | none | none |
| Bleeding disorder/blood disease/cancer | none | none | none | none | none | none | none | none | none |
| WBC in whole blood (K/µl) | 3.44 | 3.94 | 7.91 | 4.87 | 6 | 5.75 | 4.08 | 5.5 | 5.53 |
| RBC in whole blood (M/µl) | 3.71 | 4.82 | 3.54 | 4.48 | 2.77 | 3.22 | 4.67 | 3.57 | 3.66 |
| HGB in whole blood (g/dL) | 10.88 | 14.3 | 10.08 | 13.35 | 8.53 | 9.61 | 13.74 | 11.13 | 10.43 |
| HCT (%) in whole blood | 30.89 | 39.71 | 28.56 | 37.94 | 24.25 | 27.37 | 38.31 | 30.8 | 29.88 |
| Whole Blood PLT count (K/µl) | 213 | 141 | 300 | 176 | 154 | 151 | 134 | 180 | 145 |
| Whole blood vol.(ml) | 10 | 10 | 10 | 10 | 10 | 10 | 10 | 10 | 10 |
| Whole blood: PLT-Total | 2130 | 1410 | 3000 | 1760 | 1540 | 1510 | 1344 | 1803 | 1448 |
| pH of whole blood | 7.28 | 7.35 | 7.28 | 7.33 | 7.23 | 7.28 | 7.26 | 7.35 | 7.28 |
| 0 hrs:WBC in PRP (K/µl) | 0.01 | 1.3 | 0.02 | 1.1 | 3.9 | 1.4 | 3 | 4.2 | 1.1 |
| 0 hrs:RBC in PRP (M/µl) | 0.01 | 0.02 | 0.01 | 0.03 | 0.02 | 0.01 | 0.03 | 0.01 | 0.01 |
| 0 hrs:HGB in PRP (g/dL) | 0.01 | 0.01 | 0.01 | 0.01 | 0.01 | 0.01 | 0.01 | 0.01 | 0.01 |

TABLE 4-continued

| | | | | | | | | | |
|---|---|---|---|---|---|---|---|---|---|
| 0 hrs:HCT(%)in PRP | UD | UD | UD | UD | UD | UD | UD | UD | UD |
| 0 hrs:PRP: PLT count (K/µl) | 345 | 210 | 450 | 280 | 235 | 220 | 220 | 280 | 210 |
| 0 hrs:PRP vol. (ml) | 5 | 5.7 | 4.8 | 5.1 | 5.5 | 5.8 | 5.2 | 5 | 5.3 |
| 0 hrs:PRP: PLT-Total | 1725 | 1197 | 2160 | 1428 | 1293 | 1276 | 1144 | 1400 | 1113 |
| 0 hrs:Total PLT (PRP) | 1725 | 1197 | 2160 | 1428 | 1293 | 1276 | 1144 | 1400 | 1113 |
| 0 hrs:PRP = % Recovery | 0.81 | 0.85 | 0.72 | 0.81 | 0.84 | 0.85 | 0.85 | 0.78 | 0.77 |
| 0 hrs:Platelets Concentration factor | 1.62 | 1.49 | 1.50 | 1.59 | 1.53 | 1.46 | 1.64 | 1.55 | 1.45 |
| 0 hrs:pH of PRP | 7.28 | 7.35 | 7.28 | 7.33 | 7.23 | 7.28 | 7.26 | 7.35 | 7.28 |
| 4 hrs: WBC in PRP (K/µl) | 0.01 | 1.3 | 0.02 | 1.1 | 3.9 | 1.4 | 3 | 4.2 | 1.1 |
| 4 hrs:RBC in PRP (M/µl) | 0.01 | 0.02 | 0.01 | 0.03 | 0.02 | 0.01 | 0.03 | 0.01 | 0.01 |
| 4 hrs:HGB in PRP (g/dL) | 0.01 | 0.01 | 0.01 | 0.01 | 0.01 | 0.01 | 0.01 | 0.01 | 0.01 |
| 4 hrs:HCT (%) in PRP | UD | UD | UD | UD | UD | UD | UD | UD | UD |
| 4 hrs:PRP: PLT count (K/µl) | 330 | 200 | 420 | 250 | 215 | 200 | 210 | 260 | 200 |
| 4 hrs:PRP volume (ml) | 5 | 5.7 | 4.8 | 5.1 | 5.5 | 5.8 | 5.2 | 5 | 5.3 |
| 4 hrs:PRP: PLT-Total | 1650 | 1140 | 2016 | 1275 | 1183 | 1160 | 1092 | 1300 | 1060 |
| 4 hrs:Total PLT (PRP) | 1650 | 1140 | 2016 | 1275 | 1183 | 1160 | 1092 | 1300 | 1060 |
| 4 hrs:PRP = % Recovery | 0.96 | 0.95 | 0.93 | 0.89 | 0.91 | 0.91 | 0.95 | 0.93 | 0.95 |
| 4 hrs:Platelets Concentration factor | 1.55 | 1.42 | 1.40 | 1.42 | 1.40 | 1.32 | 1.56 | 1.44 | 1.38 |
| 4 hrs: pH of PRP | 7.22 | 7.2 | 7.24 | 7.23 | 7.27 | 7.21 | 7.23 | 7.23 | 7.18 |
| Ratio 4/0 hrs:PRP = % Recovery | 1.18 | 1.12 | 1.30 | 1.10 | 1.09 | 1.08 | 1.12 | 1.20 | 1.24 |
| Ratio 4/0 hrs:Platelets Concentration factor | 0.96 | 0.95 | 0.93 | 0.89 | 0.91 | 0.91 | 0.95 | 0.93 | 0.95 |
| Aggregation (Collagen) t = 0 (%) | 74 | 78 | 80 | 84.6 | 83.7 | 91.8 | 88.3 | 73.1 | 86.5 |
| Aggregation (Collagen) t = 4 h (%) | 85.2 | 82.6 | 91 | 80.2 | 86.6 | 94.7 | 80.6 | 70.9 | 81.7 |
| Hypotonic stress response t = 0 (%) | 92 | 82 | 90 | 85 | 77 | 97 | 97 | 88 | 95 |
| Hypotonic stress response t = 4 h (%) | 90 | 94 | 81 | 78 | 83 | 91 | 89 | 93 | 94 |
| P-selectin expression t = 0, resting (%) | 6.34 | 12.57 | 13.45 | 10.8 | 11.5 | 13.1 | 5.72 | 17.3 | 11.69 |
| P-selectin expression t = 0, ADP (%) | 79.56 | 64.2 | 83.8 | 66.9 | 81 | 75 | 87.61 | 83.21 | 86.91 |
| P-selectin expression t = 4 h, resting (%) | 5.32 | 12.9 | 11.6 | 13.7 | 15.2 | 18.4 | 15.78 | 6.96 | 13.19 |
| P-selectin expression t = 4 h, ADP (%) | 63.3 | 75.4 | 76.9 | 84.5 | 71.8 | 82.3 | 87.91 | 82.15 | 87.08 |
| VEGF (pg/ml)-PPP(non-activated)t = 0 | 35 | 70 | 115 | 55 | 85 | 90 | 25 | 40 | 35 |
| VEGF (pg/ml)-PRP (thrombin-activated)t = 0 | 220 | 170 | 280 | 190 | 320 | 180 | 150 | 215 | 135 |
| EGF (pg/ml)-PPP (non-activated)t = 0 | 45 | 80 | 65 | 50 | 75 | 115 | 25 | 60 | 130 |
| EGF (pg/ml)-PRP(thrombin-activated)t = 0 | 140 | 180 | 290 | 480 | 290 | 310 | 230 | 170 | 490 |
| PDGF-BB (pg/ml)-PPP(non-activated)t = 0 | 110 | 155 | 320 | 490 | 350 | 215 | 310 | 450 | 270 |
| PDGF-BB (pg/ml)-PPRO(thrombin-activated)t = 0 | 2700 | 2300 | 2900 | 1900 | 2800 | 1700 | 1300 | 2200 | 1650 |

| | Sample number | | |
|---|---|---|---|
| | 10 | 11 | 12 |
| Name initials | LM | YK | DKA |
| age | 35 | 60 | 61 |
| gender | F | M | M |
| weight | 64 | 73 | 96 |

TABLE 4-continued

|  |  |  |  |  |  |  |
|---|---|---|---|---|---|---|
| medications | none | none | none | mean | SD |  |
| Bleeding disorder/blood disease/cancer | none | none | none |  |  |  |
| WBC in whole blood (K/μl) | 4.1 | 8.5 | 7.38 | 5.583333 | 1.641038 |  |
| RBC in whole blood (M/μl) | 3.7 | 4.22 | 4.21 | 3.880833 | 0.609119 |  |
| HGB in whole blood (g/dL) | 11.29 | 12.93 | 12.96 | 11.6025 | 1.820345 |  |
| HCT (%) in whole blood | 32.55 | 37.37 | 36.97 | 32.88333 | 5.040926 |  |
| Whole Blood PLT count (K/μl) | 100 | 198 | 149 | 170 | 51 |  |
| Whole blood vol.(ml) | 10 | 10 | 10 | 10 | 0 |  |
| Whole blood: PLT-Total | 1001 | 1979 | 1490 | 1701.25 | 507.7287 | 0 |
| pH of whole blood | 7.33 | 7.23 | 7.28 |  |  |  |
| 0 hrs:WBC in PRP (K/μl) | 2.3 | 1 | 2.7 |  |  |  |
| 0 hrs:RBC in PRP (M/μl) | 0.02 | 0.01 | 0.01 |  |  |  |
| 0 hrs:HGB in PRP (g/dL) | 0.01 | 0.01 | 0.01 |  |  |  |
| 0 hrs:HCT(%)in PRP | UD | UD | UD |  |  |  |
| 0 hrs:PRP: PLT count (K/μl) | 180 | 290 | 230 |  |  |  |
| 0 hrs:PRP vol. (ml) | 5.1 | 5.6 | 5.5 |  |  |  |
| 0 hrs:PRP: PLT-Total | 918 | 1624 | 1265 | 0 | 0 | 0 |
| 0 hrs:Total PLT (PRP) | 918 | 1624 | 1265 | 0 | 0 | 0 |
| 0 hrs:PRP = % Recovery | 0.92 | 0.82 | 0.85 | 0.82 | 0.05 | #DIV/0! |
| 0 hrs:Platelets Concentration factor | 1.80 | 1.47 | 1.54 | 1.55 | 0.10 | #DIV/0! |
| 0 hrs:pH of PRP | 7.33 | 7.23 | 7.28 |  |  |  |
| 4 hrs: WBC in PRP (K/μl) | 2.3 | 1 | 2.7 |  |  |  |
| 4 hrs:RBC in PRP (M/μl) | 0.02 | 0.01 | 0.01 |  |  |  |
| 4 hrs:HGB in PRP (g/dL) | 0.01 | 0.01 | 0.01 |  |  |  |
| 4 hrs:HCT (%) in PRP | UD | UD | UD |  |  |  |
| 4 hrs:PRP: PLT count (K/μl) | 165 | 270 | 210 |  |  |  |
| 4 hrs:PRP volume (ml) | 5.1 | 5.6 | 5.5 |  |  |  |
| 4 hrs:PRP: PLT-Total | 842 | 1512 | 1155 | 0 | 0 | 0 |
| 4 hrs:Total PLT (PRP) | 842 | 1512 | 1155 | 0 | 0 | 0 |
| 4 hrs:PRP = % Recovery | 0.92 | 0.93 | 0.91 | 0.93 | 0.02 | #DIV/0! |
| 4 hrs:Platelets Concentration factor | 1.65 | 1.36 | 1.41 | 1.44 | 0.09 | #DIV/0! |
| 4 hrs: pH of PRP | 7.18 | 7.24 | 7.24 |  |  |  |
| Ratio 4/0 hrs:PRP = % Recovery | 1.00 | 1.13 | 1.08 |  |  |  |
| Ratio 4/0 hrs:Platelets Concentration factor | 0.92 | 0.93 | 0.91 |  | mean | SD |
| Aggregation (Collagen) t = 0 (%) | 70.2 | 84.4 | 71.1 |  | 80.475 | 7.16521 |
| Aggregation (Collagen) t = 4 h (%) | 70.5 | 104 | 70.7 |  | 83.225 | 10.12864 |
| Hypotonic stress response t = 0 (%) | 82 | 97 | 93 |  | 89.58333 | 6.801849 |
| Hypotonic stress response t = 4 h (%) | 94 | 98 | 94 |  | 89.91667 | 6.126816 |
| P-selectin expression t = 0, resting (%) | 12.6 | 11.49 | 17.41 |  | 11.9975 | 3.501631 |
| P-selectin expression t = 0, ADP (%) | 86.38 | 77.59 | 75.97 |  | 79.01083 | 7.561024 |

TABLE 4-continued

| | | | | | |
|---|---|---|---|---|---|
| P-selectin expression t = 4 h, resting (%) | 17.23 | 13.4 | 24.73 | 14.03417 | 5.067726 |
| P-selectin expression t = 4 h, ADP (%) | 77.51 | 77.33 | 79.13 | 78.77583 | 6.848091 |
| VEGF (pg/ml)-PPP(non-activated)t = 0 | 150 | 75 | 100 | 72.91667 | 37.50505 |
| VEGF (pg/ml)-PRP (thrombin-activated)t = 0 | 290 | 125 | 370 | | |
| EGF (pg/ml)-PPP (non-activated)t = 0 | 55 | 45 | 140 | 73.75 | 36.3146 |
| EGF (pg/ml)-PRP(thrombin-activated)t = 0 | 215 | 140 | 295 | 269.1667 | 117.5669 |
| PDGF-BB (pg/ml)-PPP(non-activated)t = 0 | 180 | 390 | 460 | 308.3333 | 125.8125 |
| PDGF-BB (pg/ml)-PPRO(thrombin-activated)t = 0 | 980 | 1450 | 2700 | 2048.333 | 645.7812 |

HGB = Hemoglobin in whole blood;
HCT = Hematocrit
UD = undetectable

Results presented in Table 4 indicate that exemplary embodiments of the invention can be used to obtain PRP comprising WBC in the range of 0.001 to 250, 0.01 to 250, 0.02 to 250, 0.1 to 250, 1 to 250, 1.1 to 250, 1.3 to 250, 2 to 250, 2.3 to 250, 3 to 250, 3.9 to 250 or 4.2 to 250 (K/μL).

Alternatively or additionally, Results presented in Table 4 indicate that exemplary embodiments of the invention can be used to obtain PRP comprising WBC in the range of 0.001 to 100, 0.01 to 100, 0.02 to 100, 0.1 to 100, 1 to 100, 1.1 to 100, 1.3 to 100, 2 to 100, 2.3 to 100, 3 to 100, 3.9 to 100 or 4.2 to 100 (K/μL). Yet another exemplary embodiment of present invention can be used to obtain PRP comprising WBC in the range of 0.001 to 25, 0.01 to 25, 0.02 to 25, 0.1 to 25, 1 to 25, 1.1 to 25, 1.3 to 25, 2 to 25, 2.3 to 25, 3 to 25, 3.9 to 25 or 4.2 to 25 (K/μL).

Alternatively or additionally, Results presented in Table 4 indicate that exemplary embodiments of the invention can be used to obtain PRP comprising WBC in the range of 0.001 to 5, 0.01 to 5, 0.02 to 5, 0.1 to 5, 1 to 5, 1.1 to 5, 1.3 to 5, 2 to 5, 2.3 to 5, 3 to 5, 3.9 to 5 or 4.2 to 5 (K/μL). Another exemplary embodiment of the invention can be used to obtain PRP comprising WBC in the range of 5 to 10, 5 to 25, 10 to 50 or 25 to 250 (K/μL). In some embodiments, the assembly for PRP can be used to deplete white blood cell content from PRP.

It should be noted that the methods, kits and assemblies of exemplary embodiments of the invention can also be used to obtain preparations of PRP having increased platelet derived growth factor content in comparison to preparations of PRP not being subjected to WBC filtration. These platelet derived growth factor can be selected for the group consisting PDGF, EGF and VEGF. In some embodiments, the methods, kits and assemblies for preparing PRP of the described exemplary embodiments can be used to obtain preparations of PRP comprising VEGF in the range of 135 to 500, 150 to 500, 190 to 500, 220 to 500, 280 to 500, 370 to 500, 135 to 370, 150 to 370, 190 to 370, 220 to 370 or 280 to 370 pg/ml. In other embodiments, the methods, kits and assemblies for preparing PRP of the described exemplary embodiments can be used to obtain preparations of PRP comprising EGF in the range of 140 to 500, 215 to 500, 310 to 500 or 215 to 310 pg/ml. In other embodiments, the methods, kits and assemblies for preparing PRP of the described exemplary embodiments can be used to obtain preparations of PRP comprising PDGF (such as PDGF—BB) as in the range of 980 to 3000, 980 to 2700, 1300 to 2700 or 1700 to 2700 pg/ml.

The selection of WBC content within the prepared PRP can be controlled, for example, by using an elongated filter device comprising pores having a varying size, cutoff size or mean pore sizes. In this respect, the pore sizes can be selected from 5 μm, 7 μm, 8 μm, 10 μm, 12 μm, 14 μm, 17 μm, 20 μm, or 23 μm. Optionally, centrifugation prior to filtration contributes to a reduction in clogging of filter pores. In summary, results presented in table 4, confirm that Exemplary embodiments of the invention are suitable for preparation of PRP in a practitioner's treatment settings.

Example 5

Blood sample analysis was conducted in the Rosenblatt Clinical Laboratories, Tel Aviv, Israel. Using an assembly for preparing platelet-rich plasma (PRP) of the kind shown in FIGS. 1A-1D, WBC-selective PRP was obtained as follows. 2 samples of about 10 ml of whole Blood were drawn from each of 4 individuals into 2 test tubes. The test tubes included a barrier-forming gel holding a vacuum. The whole blood obtained was mixed in the test tubes. The test tubes containing the mixture were centrifuged for 8 minutes at 1500 g. More than half of the plasma was removed by decantation to deplete platelet poor plasma from the test tubes. The remaining plasma above the gel barrier was vibrated to suspend the platelet pellet. A filter sleeve comprises pores having a cutoff size of 10 microns was pushed into each of the test tubes so as actuate filtration. WBC-selective PRP accumulated within the lumen of the sleeve and was withdrawn by a syringe with an attached needle. The samples of each individual were withdrawn into a tube containing either ACD (acid citrate dextrose solution) or NC (buffer citrate)) Results demonstrate that the methods, kits and assemblies according to various embodiments of the invention can be used by plurality of anticoagulant substances.

Results obtained are shown in the following Table 5.

TABLE 5

| | Sample number | | | | | | | |
|---|---|---|---|---|---|---|---|---|
| | 1 | | 2 | | 3 | | 4 | |
| Name initials | TE | | AE | | LT | | SC | |
| age | 48 | | 61 | | 49 | | 45 | |
| gender | F | | M | | F | | M | |
| medications | | | ASP | | | | ASP | |
| anti coagulant | ACD | NC | ACD | NC | ACD | NC | ACD | NC |
| WBC in whole blood (K/μl) | 11.1 | 11 | 6.9 | 7.6 | 9.6 | 10 | 7.7 | 6.9 |
| Whole Blood PLT count (K/μl) (C) | 317 | 391 | 162 | 177 | 261 | 283 | 141 | 142 |
| whole blood volume (ml) | 10 | 11 | 11 | 11 | 10 | 11 | 10 | 11 |
| whole blood - Total PLT | 0.3 | 0.2 | 0.2 | 0 | 2 | 4 | 0.3 | 0 |
| WBC in PPP (K/μl) | 0.2 | 0.2 | 0.2 | 0.3 | 0.5 | 0.4 | 0.3 | 0.1 |
| PPP: PLT count (K/μl) (D) | 1.5 | 1 | 1 | 0 | 4 | 10 | 1 | 0 |
| PPP volume (ml) | 1.5 | 1.5 | 1.5 | 1.5 | 1.5 | 1.5 | 1.5 | 1.5 |
| PPP: PLT - Total (K/μl) | 643.5 | 3677.4 | 461.7 | 669.2 | 2860.9 | 1398.4 | 432.5 | 2457 |
| WBC in PRP after filter (K/μl) | 1.5 | 8.1 | 2.7 | 2.8 | 6.1 | 3.8 | 2.5 | 9.1 |
| PRP after filter: PLT count (K/μl) | 429 | 454 | 171 | 239 | 469 | 368 | 173 | 270 |
| PRP after filter volume (ml) | 6 | 6.5 | 6.6 | 6.3 | 5.5 | 6.2 | 6 | 6 |
| PRP:after filter PLT- Total | 42 | 45.5 | 46.2 | 44.1 | 38.5 | 43.4 | 42 | 42 |
| pH of PRP after filter | 7 | 7 | 7 | 7 | 7 | 7 | 7 | 7 |
| Total PLT (PPP + PRP after filter) | 6 | 6.5 | 6.6 | 6.3 | 5.5 | 6.2 | 6 | 6 |

The invention claimed is:

1. An assembly for preparing platelet rich plasma (PRP) having a reduced white blood cell (WBC) content comprising:
   a. a test tube for receiving a blood sample or a platelet-comprising fraction thereof and for obtaining therein, by a procedure that includes centrifugation, a platelet rich plasma (PRP) fraction;
   b. an elongated sliding filter device having a first and second end and a lumen extending there between, and having a filter fitted at the first end, said filter having an effective pore size of about 5-25 μm such to permit passage of platelets and not permit passage of white blood cells (WBC) larger than a defined size into the lumen, the second end having an opening; said first end of the elongated filter device being adapted for tight fitting into said test tube such that when forced into the test tube to exert pressure on the PRP fraction, the PRP fraction with the platelets filters into said lumen and white blood cells of a size larger than said defined size remains in the test tube to thereby obtain a WBC-selective PRP within said lumen.

2. The assembly of claim 1, wherein said tight fitting is achieved by an elastomeric ring element fitted on the external wall of the first end of said elongated filter device.

3. The assembly of claim 1, wherein said elongated filter device has a frustoconical shape with a broad first end tapering towards the second end.

4. The assembly of claim 1, comprising a grip element for fitting around external walls of said elongated filter device.

5. The assembly of claim 4, wherein said grip is adapted to engage with said elongated filter device and said test tube to thereby limit the forced movement of the first end of the elongated filter device into said tube or wherein said grip is fitted over said second end and having leading edge with internal diameter identical to external diameter of said elongated filter device in a mid-portion thereof between the two ends.

6. The assembly of claim 5, having a portion of at least said leading end that can engage with a rim of said tube to thereby limit the forced movement of the first end of the elongated filter device into said tube or wherein the opening at said second end permits a syringe access for withdrawal of the WBC-selective PRP from said lumen.

7. The assembly of claim 1, wherein said filter comprises pores having a cutoff size of no more than approximately 5 μm, 7 μm, 8 μm, 10 μm, 12 μm, 14 μm, 17 μm, 20 μm, or 23 μm and wherein said assembly comprises a slider filter member of specific density between about 1.03-1.08; further wherein the said test tube has openings at its two ends fitted with stoppers.

8. The assembly of claim 1, wherein said filter device comprises: a sleeve with a filter in its base, the filter having a pore size of about 5-25 μm which permits passage of platelets but does not permit passage of at least a selected fraction of white blood cells (WBC) and adapted to:
   i. circumferentially contact an inner wall of a test tube; and
   ii. slidingly descend into said test tube in response to an applied pressure.

9. The assembly according to claim 1, further comprising:
   a. a collection tube adapted to receive blood or a blood fraction including platelets; and,
   b. a sliding filter member adapted for fluid-tight contact with inner walls of the test tube and slidable axially into the test tube and fitted with a filter having a pore size of about 5-25 μm which permits passage of platelets but does not permit passage of at least a selected fraction of white blood cells (WBC); wherein said filter member is characterized by a specific gravity selected so that during centrifugation at a defined g-force it descends into said blood or fraction to produce platelet-rich plasma (PRP) above said filter.

10. The assembly of claim 1, wherein said test tube for receiving blood further comprises a barrier-forming substance; said barrier is a gel polymer, selected from the group consisting of: polyacrylic, polyolefin, polyester and a mixture thereof.

11. The assembly of claim 10, wherein said gel has a specific gravity in a range of about 1.03 to 1.08.

12. A method of preparing platelet rich plasma (PRP) having a reduced white blood cell content (WBC-selective PRP), comprising:
  i. providing an assembly for preparing platelet rich plasma (PRP) having a reduced white blood cell content comprising:
    a. a test tube for receiving a blood sample or a platelet-comprising fraction thereof and for obtaining therein, by a procedure that includes centrifugation, a platelet rich plasma (PRP) fraction and
    b. an elongated sliding filter device having a first and second end and a lumen extending there between, and having a filter fitted at the first end, said filter having a effective pore size of about 5-25 µm such to permit passage of platelets and not permit passage of white blood cells (WBC) larger than a defined size into the lumen, the second end having an opening; said first end of the elongated filter device being adapted for tight fitting into said test tube such that when forced into the test tube to exert pressure on the PRP fraction, the PRP fraction with the platelets filters into said lumen and white blood cells of a size larger than said defined size remain in the test tube to thereby obtain a WBC-selective PRP within said lumen;
  ii. introducing blood or a platelet-comprising blood fraction into said assembly;
  iii. centrifuging said test tube having said sliding filter device, said filter is with an effective pore size such to permit passage of platelets and not permit passage of white blood cells (WBC) larger than a defined size, the test tube containing whole blood obtained from a subject, thereby obtaining a platelet poor plasma (PPP) fraction, a platelet rich plasma (PRP) fraction and optionally a platelet pellet.

13. The method according to claim 12, further comprising activating the platelets in said WBC-selective PRP.

14. The method according to claim 12, wherein said centrifuging said assembly is for obtaining a blood fraction rich with platelets and having a reduced white blood cell content above the filter member.

15. The method of claim 12, further comprising:
  a. removing the platelet poor plasma (PPP) from the test tube; and
  b. suspending the remaining platelet content of the test tube.

16. The method of claim 12, further comprising activating by mixing the obtained platelet rich plasma (PRP) with an activating agent selected from the group consisting of Thrombin, $CaCl_2$, collagen, ADP or combination thereof.

17. The method of claim 12, wherein said PRP is autologous PRP.

18. The method according to claim 12, further comprising suspending the platelet pellet in the PRP; thereby obtaining a WBC-selective PRP.

19. The method of claim 12, wherein said method additionally comprises a step of providing said test tube comprising a barrier-forming substance; said barrier comprising a gel polymer selected from the group consisting of: polyacrylic, polyolefin, polyester and a mixture thereof.

20. The method of claim 12, wherein said method additionally comprises the step of providing said test tube that further comprises a gel polymer with a specific gravity in a range of about 1.03 to 1.08.

21. A kit for preparing platelet rich plasma (PRP) having a reduced white blood cell content (WBC-selective PRP), for use in treating a subject with the WBC-selective PRP wherein the treatment is at least one selected from the group consisting of wound healing, PRP injection to the skin, biological glue, cosmetic treatment, skin regeneration treatment and anti-aging treatment further wherein said PRP is autologous PRP, the kit comprising:
  a. an assembly according to claim 1; and,
  b. instructions for a method of preparing platelet rich plasma (PRP), the method comprising: pre-treating a blood sample to produce a platelet poor plasma (PPP) fraction, a platelet rich plasma (PRP) fraction and, optionally, a platelet pellet.

22. The kit according to claim 21, additionally comprising said instructions for:
  a. optionally, suspending the platelet pellet in the PRP; and
  b. in a test tube of said assembly, causing the filter having a pore size of about 5-25 µm which permits passage of platelets but does not permit passage of at least a selected fraction of white blood cells (WBC) circumferentially to contact an inner wall of a test tube and slidingly descend into said test tube so that a WBC depleted PRP fraction accumulates above the filter.

* * * * *